United States Patent [19]

Jones et al.

[11] Patent Number: 5,753,476
[45] Date of Patent: May 19, 1998

[54] IDENTIFICATION OF A HUMAN CYTOMEGALOVIRUS GENE REGION INVOLVED IN DOWN REGULATION OF MHC CLASS I HEAVY CHAIN EXPRESSION

[75] Inventors: Thomas R. Jones, Nyack, N.Y.; Ann E. Campbell, Norfalk, Va.

[73] Assignee: American Cyanamid Company, Madison, N.J.

[21] Appl. No.: 458,544

[22] Filed: Jun. 2, 1995

Related U.S. Application Data

[62] Division of Ser. No. 282,696, Jul. 29, 1994.

[51] Int. Cl.⁶ .......................... C12N 15/64; C12N 15/10; C12N 7/04
[52] U.S. Cl. ..................... 435/172.3; 435/91.42; 435/236
[58] Field of Search ............... 435/172.1, 172.3, 435/236, 91.32, 91.33, 91.42; 424/230.1

[56] References Cited

FOREIGN PATENT DOCUMENTS

| 0521427 | 1/1993 | European Pat. Off. |
| WO89/10966 | 11/1989 | WIPO |

OTHER PUBLICATIONS

Kollert, Jons A. et al., J. Virology, vol. 65, No. 10, 1991, pp. 5184–5189.
Jones, T.R. et al., J. Virology, vol. 66, No. 4, 1992, pp. 2541–2546.
Chee M.S. et al., Current Topics in Microbiology and Immunology, vol. 154, 1990, pp. 126–169.
Gilbert, M.J. et al., J. Virology, vol. 67, No. 6, 1993, pp. 3461–3469.
Beersma, M.F.C. et al., J. Immunology, vol. 151, No. 9, 1993, pp. 4455–4464.
Jones, T.R. et al., J. Virology, vol. 69, No. 8, 1995, pp. 4830–4841.
Colberg-Poley, A. M. et al., J. Virology, vol. 66, No. 1, 1992, pp. 95–105.

*Primary Examiner*—George C. Elliott
*Assistant Examiner*—Terry A. McKelvey
*Attorney, Agent, or Firm*—Elizabeth M. Barnhard

[57] ABSTRACT

Infection of human fibroblast cells with human cytomegalovirus (HCMV) causes down regulation of cell surface expression of MHC class I. The present invention is directed to a mutant with a 9-kb deletion in the S component of the HCMV genome (including open reading frames IRS1–US9 and US11) which failed to down regulate class I heavy chains. By examining the phenotypes of mutants with smaller deletions with this portion of the HCMV genome, a 7-kb region containing at least 9 open reading frames was shown to contain the genes required for reduction in heavy chain expression. Furthermore, it was determined that two subregions (A and B) of the 7-kb region each contained genes which were sufficient to cause heavy chain down regulation. In subregion B, the US11 gene product is involved. It encodes a endoglycosidase H-sensitive glycoprotein which is intracytoplasmic, similar to the adenovirus type 2 E3-19K glycoprotein which inhibits surface expression of class I heavy chains.

5 Claims, 17 Drawing Sheets

RV7186 (IRS1-US11 DELETED)

RV798 (US2-US11 DELETED)

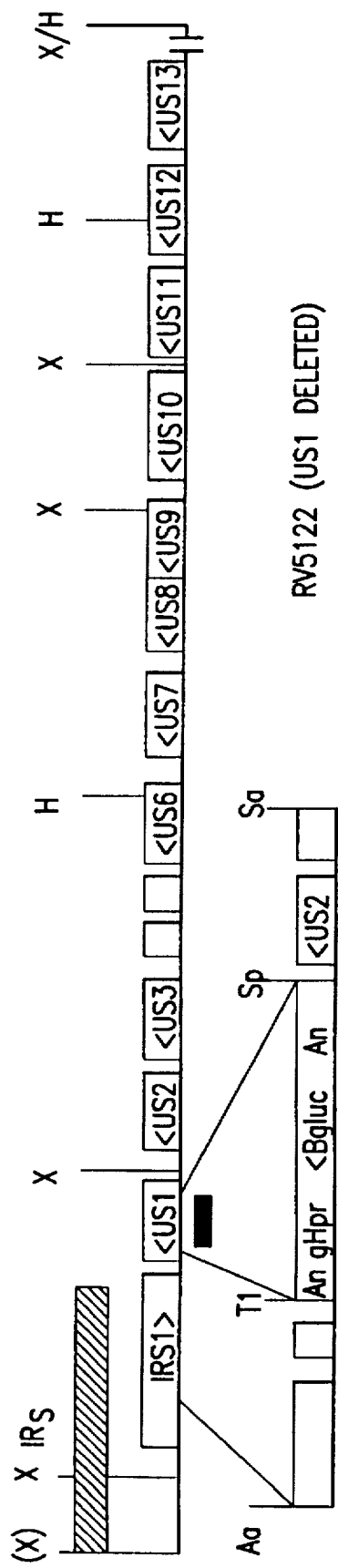
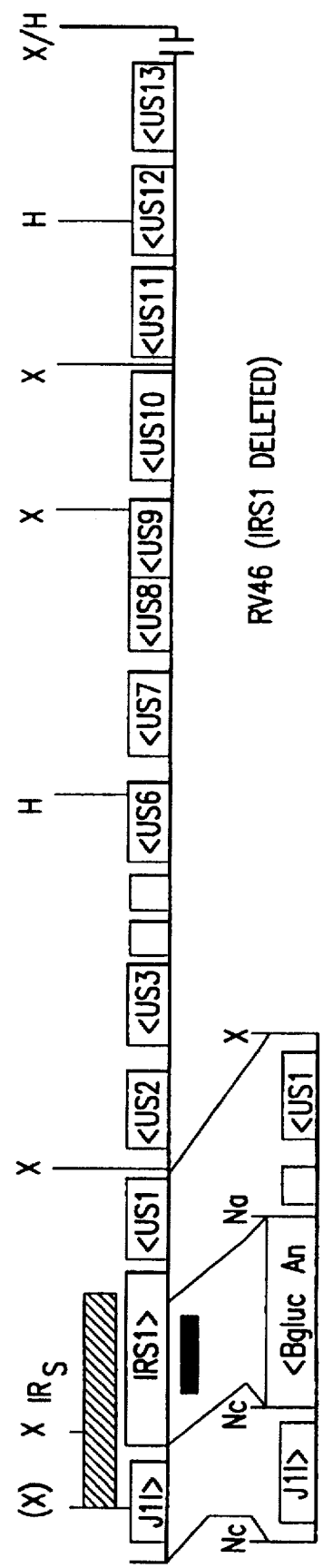
FIG. 3H
FIG. 3I

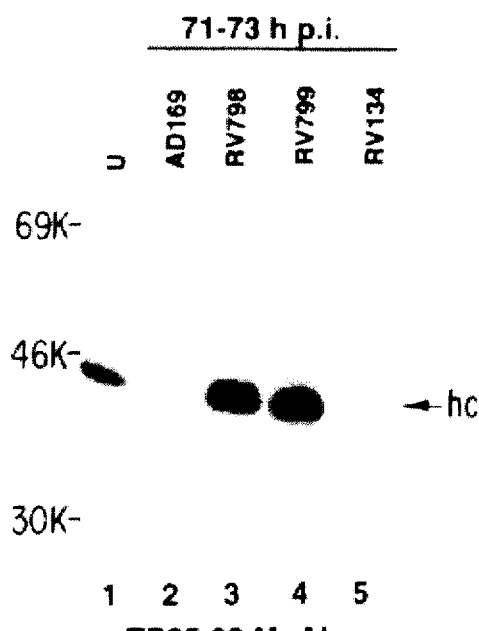
FIG. 5A
FIG. 5C
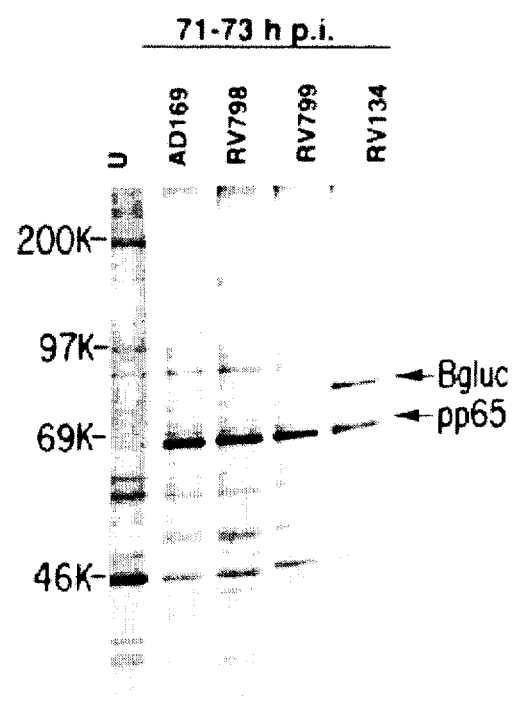
FIG. 5B

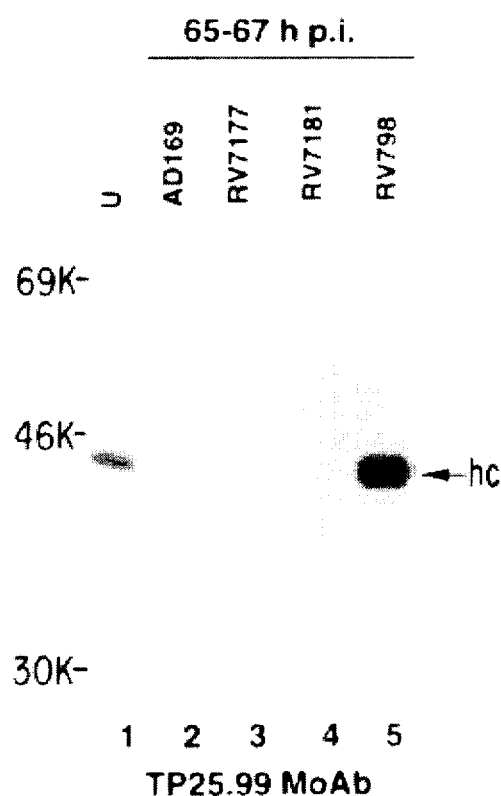
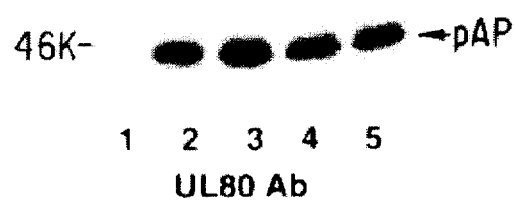
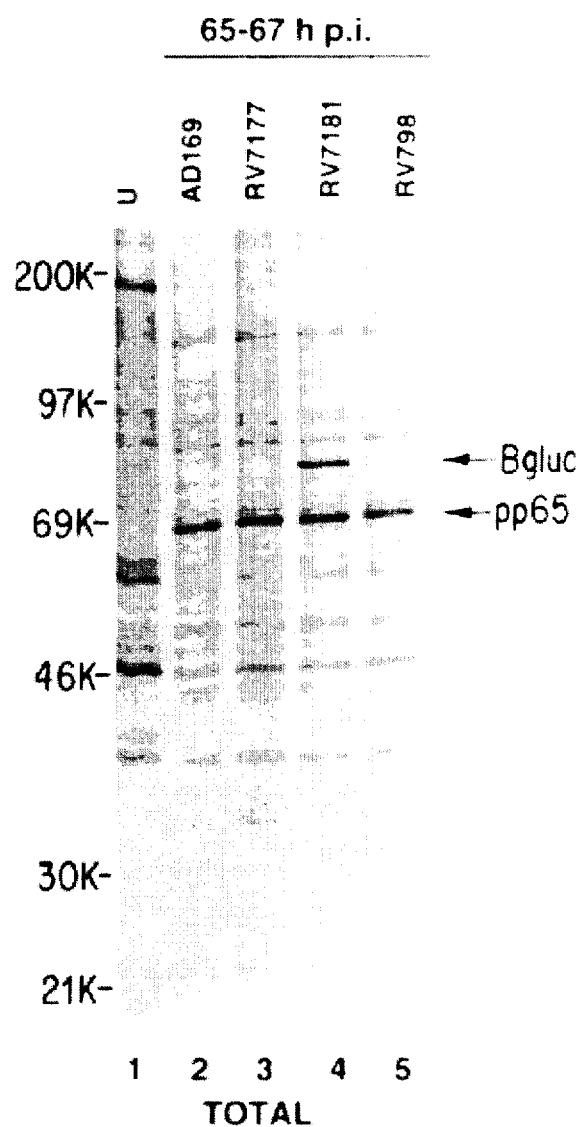
FIG. 7A
FIG. 7C
FIG. 7B

PERMEABILIZED

AD169 (WT) 8h p.i.

NONPERMEABILIZED

AD169 (WT) 8h p.i.

RV699 8h p.i.

RV699 8h p.i.

IDENTIFICATION OF A HUMAN CYTOMEGALOVIRUS GENE REGION INVOLVED IN DOWN REGULATION OF MHC CLASS I HEAVY CHAIN EXPRESSION

This is a divisional of copending application Ser. No. 08/282,696 filed on Jul. 29, 1994.

FIELD OF THE INVENTION

The present invention relates to recombinant mutant human cytomegalovirus (HCMV) which does not down regulate expression of cellular MHC class I heavy chains upon infection.

BACKGROUND OF THE INVENTION

Human cytomegalovirus (HCMV) is a betaherpesvirus which causes clinically serious disease in immunocompromised and immunosuppressed adults, as well as in some infants infected in in utero or perinatally (Alford and Britt, 1990). The 230-kb dsDNA genome of HCMV was sequenced (Chee et al., 1990) and has at least 200 open reading frames (ORFs). For purposes of this application, open reading frame is defined as the portion of a gene which encodes a string of amino acids and hence may encode a protein. The function of some HCMV proteins are known or predicted due to their homology with other viral (esp. herpes simplex virus) and cellular proteins. However, for the majority of the HCMV ORFs, the function(s) of the proteins they encode is unknown.

In order to study HCMV gene function HCMV deletion mutants can be constructed in order to assess their in vitro growth properties (Jones et al., 1991; Jones and Muzithras, 1992). For purposes of this application deletion mutants are defined as human cytomegalovirus mutants which lack regions of the wild-type viral genome. This strategy involves site-directed replacement mutagenesis of selected HCMV gene(s) by a prokaryotic reporter gene, usually β-glucuronidase, although guanosine phosphoribosyltransferase can also be used. In this fashion, the recombinant virus can be isolated only if the replaced viral gene(s) is nonessential.

Several investigators have shown that infection by HCMV results in the down regulation of cellular MHC class I heavy chains (Browne et al., 1990; Beersma et al., 1993; Yamashita et al., 1993). For purposes of this application, down regulation is defined as reduction in either synthesis, stability or surface expression of MHC class I heavy chains. Such a phenomenon has been reported for some other DNA viruses, including adenovirus, murine cytomegalovirus, and herpes simplex virus (Anderson et al., 1985; Burget and Kvist, 1985; del Val et al., 1989; Campbell et al., 1992; Campbell and Slater, 1994; York et al., 1994). In the adenovirus and herpes simplex virus systems, the product of a viral gene which is dispensable for replication in vitro is sufficient to cause down regulation of MHC class I heavy chains (Anderson et al., 1985; Burget and Kvist, 1985). The gene(s) involved in class I heavy chain down regulation by murine cytomegalovirus have not yet been identified.

SUMMARY OF THE INVENTION

The present invention is directed to a recombinant mutant human cytomegalovirus which does not down regulate expression of cellular MHC class I heavy chains upon infection. Mutants RV 798 and RV 799 both deleted of open reading frames US2–US11, lose the ability to down regulate MHC class I heavy chains.

The present invention is also directed to a method to produce the recombinant mutant human cytomegalovirus and a vaccine which utilizes the cytomegalovirus. One skilled in the art will use live attenuated HCMV vaccine lacking this gene region in order to elicit a better immune response, than one containing this gene region, based on the lack of class I down registration by the former. Therefore a virus lacking the region is a superior immunogen.

In addition, the HCMV gene involved in the MHC class I heavy chain down regulation can be incorporated into adenovirus vectors or similar virus based gene therapy vectors to minimize the immune response which will allow the use of the recombinant adenovirus or similar virus based gene therapy vectors to be used in gene therapy.

The invention may be more fully understood by reference to the following drawings.

BRIEF DESCRIPTION OF THE DRAWINGS

FIG. 2A is a Western blot analysis. HFF cells were uninfected (U) or infected at a multiplicity of infection of 5 PFU/cell. At 24, 48, and 72 h postinfection total cellular proteins were harvested, electrophoresed through a 15% SDS-polyacrylamide gel, electroblotted to nitrocellulose, and probed with TP25.99 murine monoclonal antibody (specific for a non-conformational epitope on MHC class I heavy chains) using an ECL chemiluminescent detection kit (Amersham). FIGS. 2B and C are immunoprecipitation analyses. HFF cells were uninfected or infected (as above), either in the absence or presence (+PFA) of phosphonoformate and radiolabeled either for 4 h at late times postinfection (69–73 h) (FIG. 2B) or for 2 h at the indicated time postinfection (FIG. 2C). Proteins were harvested immediately after radiolabeling and class I heavy chains were immunoprecipitated using TP25.99 murine monoclonal antibody.

FIGS. 3A–3J. Organization of recombinant virus genomes. FIG. 3A, the first line, is a schematic of the overall organization of the HCMV wild-type genome. Unique region sequences are shown by a line, while repeated region sequences are indicated by shaded boxes. Relevant HindIII fragments, within the L and S components, are indicated by letter designation (Oram et al., 1982). The second line is an expansion of the wild-type HindIII-Q, -X, and -V regions of the S component. The significant open reading frames, and their orientation, are shown as open boxes (Chee et al., 1990). The position of the IRs repeated sequences is indicated by the shaded rectangle. The locations of HindIII (H) and XhoI (X) restriction endonuclease sites are shown. FIGS. 3B–I show the genomic organization of the indicated HCMV mutant. In each case, the first line is the organization of the AD169 wild-type genome, the second line represents the organization of relevant sequences of the linearized plasmid used to make the recombinant virus. The slanted lines indicate the boundaries of the viral flanking sequences which may be involved in homologous recombination to create the desired mutation. The region deleted is indicated by a shaded box below the first line. FIG. 3J shows the derivation and organization of RV799. The first two lines are the same representations as FIGS. 3B–I, and the third line represents the organization of the relevant sequences of the linearized plasmid used to make RV799 from the RV134 parent (second line).

FIG. 4A is a radiograph of Class I heavy chains which were immunoprecipitated using TP25.99 murine monoclonal antibody. FIG. 4B is a radiograph of total radiolabeled proteins to verify approximately equivalent radiolabeling efficiency. FIG. 4C is a radiograph to verify equal progression through the viral replicative cycles. UL80 proteins were immunoprecipitated using anti-assembly protein rabbit polyclonal antiserum.

FIGS. 5A–5C shows immunoprecipitation of class I heavy chains from RV798-, RV799-, RV134-, or AD169 wild-type-infected cells. HFF cells were uninfected (U) or infected with the indicated virus (multiplicity of infection of 5 PFU/cell) and radiolabeled for 2 h at late times postinfection (71–73 h). Proteins were harvested immediately after radiolabeling. FIG. 5A is a radiograph of Class I heavy chains which were immunoprecipitated using TP25.99 murine monoclonal antibody. Equivalent radiolabeling efficiency (FIG. 5B) and progression through the viral replicative cycle (FIG. 5C) were verified as described for FIGS. 4B and 4C.

FIGS. 7A–7C show the immunoprecipitation of class I heavy chains from RV798-, RV7181-, RV7177-, or AD169 wild-type-infected cells. HFF cells were uninfected, (U) or infected with the indicated virus (multiplicity of infection of 5 PFU/cell) and radiolabeled for 2 h at late times postinfection (65–67 h). Proteins were harvested immediately after radiolabeling. FIG. 7A is a radiograph of Class I heavy chains which were immunoprecipitated using TP25.99 murine monoclonal antibody. Equivalent radiolabeling efficiency (FIG. 7B) and progression through the viral replicative cycle (FIG. 7C) were verified as described for FIGS. 4B–C.

FIG. 9A is a radiograph of Class I heavy chains were immunoprecipitated using TP25.99 murine monoclonal antibody. FIG. 9B is a radiograph in which, to verify approximately equal infection, the 72-kDa IE1 immediate-early protein was immunoprecipitated using the murine monoclonal antibody 9221. FIG. 9C is a radiograph of the immunoprecipitation of the cellular transferrin receptor with murine monoclonal antibody Ber-T9 to verify approximately equal expression of this glycoprotein. FIG. 9D is a radiograph of total radiolabeled proteins to verify approximately equivalent radiolabeling efficiency.

In FIG. 10, the first line is the overall organization of the HCMV wild-type genome, and the second line is an expansion of the wild-type HindIII-Q and -X regions of the S component. The ORFs are indicated by an unshaded rectangle; the unlabeled ORF overlapping US4 and US5 is US4.5. In FIG. 10, the deletions within the various HCMV mutants are indicated by the shaded rectangle. RV670 is deleted of IRS1–US9 and US11; RV35 is deleted of US6–US11; RV67 is deleted of US10–US11; RV80 is deleted of US8–US9; RV725 is deleted of US7; RV69 is deleted of US6; RV47 is deleted of US2–US3; RV5122 is deleted of US1; RV46 is deleted of IRS1; RV798 is deleted of US2–US11; RV7181 is deleted of IRS1–US9; RV7177 is deleted of IRS1–US6; and RV7186 is deleted of IRS1–US11. MHC class I heavy chain down regulation results are from immunoprecipitation experiments (using the heavy chain conformation-independent monoclonal antibody, TP25.99) in which HCMV-infected HFF cells were radiolabeled at late times postinfection. FIG. 10 shows location of the two subregions which contain gene(s) which are sufficient for MHC class I heavy chain down regulation. Subregion A contains ORFs US2–US5 (bases 193119–195607) and subregion B contains ORFs US10 and US11 (bases 199083–200360).

DESCRIPTION OF THE PREFERRED EMBODIMENTS

Figure 1A:
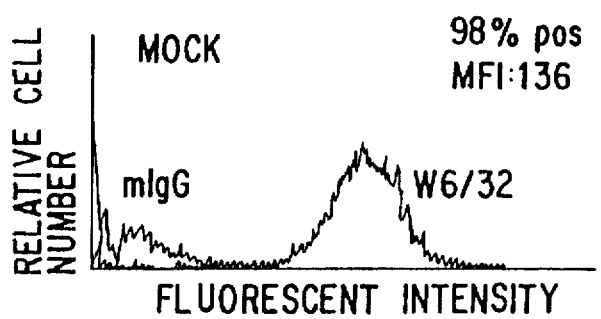
FIG. 1. Detection of cell surface MHC class I by immunofluorescence-flow cytometry in HCMV-infected cells. Human foreskin fibroblast (HFF) cells were infected with the indicated virus at a multiplicity of infection of 5 PFU/cell for 72 h. At that time, cells were fixed in 1% paraformaldehyde and stained with primary antibody specific for HLA-A, B, C (W6/32) or control mouse IgG (isotype matched) followed by secondary FITC-conjugated goat anti-mouse IgG. Percent positive cells ($5 \times 10^3$ total) and mean fluorescent intensity (MFI) were calculated on the basis of forward angle light scatter versus log-integrated 90° light scatter using the Immuno Program, Coulter MDADS I.
Figure 1B:
Figure 1C:
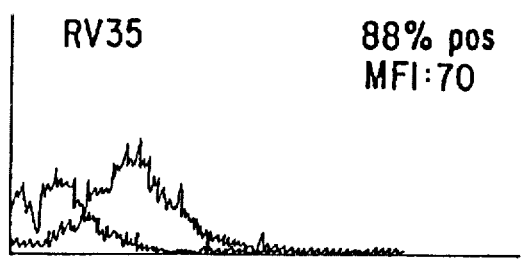
Figure 1D:
Figure 1E:
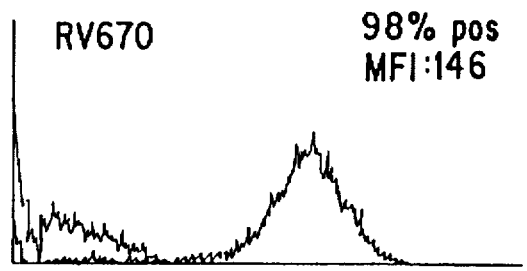

A recombinant HCMV mutant called RV670, has been constructed which expresses a marker gene (β-glucuronidase) in place of a group of viral genes. Upon infection of human fibroblast cells with this mutant, it is demonstrated that expression of the major histocompatibility complex (MHC) class I heavy chains are not reduced, as it is when wild-type HCMV infects these cells.

Unlike wild-type HCMV, the present invention's virus does not result in the down regulation of cellular MHC class I heavy chain protein expression. A 7 kb region of the HCMV genome which contains genes which are required for down regulation of heavy chain expression is utilized in the invention.

One skilled in the art will appreciate that efficient antigen processing and presentation is required to activate and expand cytotoxic T-Lymphocyte precursors for an efficient cell mediated immune response. Efficient viral antigen presentation requires the continued expression of MHC class I proteins throughout infection. Infection of cells with RV670 results in continued expression of class I heavy chains.

One skilled in the art will appreciate that the claimed virus (RV670) or another human cytomegalovirus with a deletion of similar genes, can be utilized to produce an effective live vaccine since class I heavy chains are still expressed in RV670-infected cells, as they are in uninfected cells, and therefore viral antigen presentation, for the purpose of initiating a cytotoxic T cell response occurs.

In the present invention, flow cytometry and immunofluorescence experiments confirmed that cell surface expression of class I heavy chains are greatly reduced at late times postinfection in HCMV wild-type strain 8169 infected HFF cells. Radiolabeling-immunoprecipitation experiments indicates that down regulation of newly synthesized MHC class I heavy chains occurs throughout the course of infection, beginning at very early times (3 h) postinfection (FIG. 2C). This reduction has been reported to be at the post-translational level: class I heavy chains have a higher turnover rate in HCMV-infected cells than in uninfected cells (Beersma et al., 1993). Such instability of class I heavy chains results in a reduced cell mediated immune response to HCMV infection since viral peptides will be inefficiently presented. Thus, the reduction in class I heavy chain expression is important in terms of evasion of host's immune system in the establishment of persistent or latent infections by HCMV (Gooding, 1992).

We screened our bank of HCMV mutants which represent 18 ORFs which are dispensable for viral replication in tissue culture for their ability to cause down regulation of MHC class I heavy chains. A 7-kb region of the S component of the HCMV genome, containing ORFs US2–US11 (bases 193119–200360), is clearly shown to contain genes which are required for this phenotype (data summarized in FIG. 10). Within this region, there are two subregions, each of which contain genes sufficient for heavy chain down regulation. Subregion A contains ORFs US2–US5 (bases 193119–195607). It is proposed that US2 and US3 encode membrane glycoproteins (Chee et al., 1990). US3 is a differentially spliced gene which is expressed throughout the viral replicative cycle and encodes a protein with transcriptional transactivating function (Tenney and Colberg-Poley, 1991; Colberg-Poley et al., 1992; Tenney et al., 1993; Weston, 1988). Several smaller ORFs are also present in this subregion (between the ORFs US3 and US5), but their expression characteristics or functions have not been reported. Gretch and Stinski (1990) reported that there is a 1.0-kb early mRNA transcribed from this region of the HCMV genome, but it was not fine-mapped. It is not yet known which of these genes are involved in heavy chain down regulation.

Subregion B is also sufficient for MHC class I heavy chain reduction contains the US10 and US11 genes (FIG. 10), bases 199083–200360. However, based on data using HCMV mutant RV670, which expresses wild-type levels of the US10 gene product (Jones et al., manuscript in preparation), US10 expression is not sufficient for down regulation of heavy chain expression (FIG. 2B). Thus, the genetic data implicates the US11 gene product as being required. We have demonstrated that US11 expression is sufficient to cause MHC class I heavy chain down regulation in stably transformed uninfected cells in the absence of other MCNV proteins. (FIG. 11) RNA and protein expression from both of these ORFs begins early and proceeds throughout the course of infection (Jones and Muzithras, 1991); US10 and US11 encode glycoproteins of 22-kDa (gpUS10) and 32-kDa, (gpUS11) respectively; both glycoproteins have N-linked sugar residues which are completely endoglycosidase H sensitive. These glycoproteins are retained in the endoplasmic reticulum or cis golgi. Consistent with this conclusion is the immunofluorescence data in which gpUS11 was not detected on the cell surface, but was detected in the cytoplasm of HCMV-infected cells (FIG. 8). The characteristics of HCMV gpUS11 (as well as gpUS10) are similar to the 25-kDa glycoprotein (E3-19K) encoded from the E3 region of adenovirus type 2. Ad E3-19K is nonessential for viral replication. It has been shown to contain endoglycosidase H-sensitive N-linked sugar residues, be retained in the endoplasmic reticulum, and bind MHC class I heavy chains; thereby preventing their transport to the cell surface 9 (Anderson et al., 1985; Burgert and Kvist, 1985). In contrast to Ad E3-19K, a direct association between gpUS11 (or gpUS10) and class I heavy chains (i.e. by coimmunoprecipitation) was not detected (data not shown).

The identification of US2–US11 gene region as the region of the HCMV genome required for down regulation of MHC class I heavy chains is significant in several respects. As mentioned above, expression from this region of the genome throughout the course of infection acts to interfere with an effective cell mediated immune response. Surface expression of MHC class I molecules is required for antigen presentation to activate and expand cytotoxic T lymphocyte (CTL) precursors populations (Schwartz, 1985). In addition, they are further required for target recognition by the activated CTLs (Zinkernagel and Doherty, 1980). In MCMV, CTLs against the major immediate-early protein are protective against lethal infection by this virus (Jonjic et al., 1988). However, in HCMV infected individuals, the frequency of CTLs against the analogous HCMV immediate-early protein, IE1, are reported to be extremely rare (Gilbert et al., 1993). Recent studies have shown that IE peptides are more efficiently presented by interferon-γ-treated HCMV-infected cells, than by untreated infected cells (Gilbert et al., 1993). Interferon μ causes increased surface expression of MHC class I proteins. Thus, increasing the expression of class I heavy chains in HCMV-infected cells may be important in the efficient generation of IE-specific CTLs, or CTLs against other important HCMV antigens. A HCMV mutant deleted of the US2–US11 gene region would have this effect since the class I heavy chains are not down regulated when cells are infected with this mutant. Therefore, a deletion of this region of the viral genome is important in the development of an live HCMV vaccine to induce an effective anti-HCMV immune response.

Several years ago it was reported that the HCMV UL18 ORF encoded a protein which resembled MHC class I heavy chains (Beck and Barrell, 1988). It was hypothesized that the down regulation of heavy chains in HCMV-infected cells was due to competition of the UL18 gene product for β2-microglobulin, which effectively prevented the normal association of class I heavy chains and β2-microglobulin (Browne et al., 1990). This hypothesis was essentially dispelled when a HCMV mutant deleted of UL18 retained its ability to down regulate heavy chain expression (Browne et al., 1992). It remained possible that the UL18 gene product was only one of several HCMV genes whose expression is sufficient for this phenotype. However, the present invention data indicates that only genes within the US2–US11 region are sufficient for class I heavy chain down-regulation.

The existence of two independent mechanisms which result in down regulation of MHC class I expression emphasizes the importance of this phenotype for successful infection and persistence in the host. One mechanism may serve as a backup system for the other, but also plausible is that there is cell type specificity for each system. In the case of the HFF cell system, both mechanisms are functional. However, in U373-MG cells, down regulation of heavy chain expression is more dependent on the presence of the subregion A. In that case, there may be qualitative or quantitative differences in cellular proteins which interact with subregion B gene products. A similar situation exists in the herpes simplex virus system. It was recently reported that the 88 amino acid US12 gene product (ICP47) is sufficient for class I heavy chain sequestering in the endoplasmic reticulum (York et al., 1994). However, expression of heavy chains is not affected in herpes simplex virus-infected mouse cells, although ICP47 is expressed in those cells and murine heavy chains are down regulated when expressed in an HSV-infected human fibroblast system (York et al., 1994).

A pharmaceutical composition may be prepared containing the recombinant HCMV mutant of the present invention in which the genome is devoid of a gene sequence capable of down regulating MHC Class I expression in infected cells. A stabilizer or other appropriate vehicle may be utilized in the pharmaceutical composition.

As discussed earlier, the recombinant HCMV mutant of the present invention which is devoid of the gene sequence capable of down regulating MHC Class I expression may be used in a vaccine for the prevention of cytomegalovirus infections. The vaccine comprises an effective amount of the recombinant HCMV mutant in a pharmaceutically acceptable vehicle. An adjuvant may be optionally added to the vaccine.

A method of immunizing an individual against cytomegalovirus may be carried out by administering to the individual an immunogenic amount of the recombinant HCMV mutant of the present invention which is devoid of the gene sequence capable of down regulating MHC Class I expression.

A method of preventing or reducing susceptibility in an individual to acute cytomegalovirus may be carried out by administering to the individual an immunogenic amount of the recombinant HCMV mutant of the present invention which is devoid of the gene sequence capable of down regulating MHC Class I expression.

Down regulation of MHC Class I expression in a cytomegalovirus infected cell may be controlled by a method having the steps of identifying a gene sequence capable of down regulating the major histocompatibility complex and deleting the identified gene sequence from the cytomegalovirus genome.

As discussed earlier, the gene sequence involved in the MHC Class I heavy chain down regulation can be incorporated into adenovirus vectors or similar virus based gene therapy vectors to minimize the immune response and allow the use of the vectors in gene therapy. One virus based gene therapy vector comprises the gene sequence of the open reading frame of US11. Another virus based gene therapy vector comprises the gene sequences of subregions A and B (open reading frames US2–US5 and US10–US11, respectively).

EXAMPLE 1

Virus and Cells. HCMV strain AD169 is obtained from the American Type Culture Collection and propagated according to standard protocols known by those skilled in the art. Human foreskin fibroblast (HFF) cells were isolated in this laboratory and used below passage twenty (Jones and Muzithras, 1991). They were grown in Dulbeccos modified Eagle medium (DMEM) containing 10% fetal bovine serum and 25 mM HEPES.

DNA sequence. The numbering system of Chee et al. (1990) of the HCMV strain AD169 DNA sequence (Genbank accession number X17403) is used in the present invention.

Plasmids. Plasmids used for creation of HCMV mutants are constructed using the method described previously (Jones et al., 1991; Jones and Muzithras; 1992). Generally, the β-glucuronidase reporter gene is surrounded on each side by 1.5-kb of HCMV sequences which flank the gene(s) to be deleted from the virus. In each case, the plasmid DNA is linearized with a restriction enzyme which cuts within the prokaryotic backbone prior to transfection. The HCMV strain AD169 genomic DNA fragments are derived from either pHind-G, pHind-X, or pXba-P which contain the HindIII-G (bases 176844 to 195837), -X (bases 195837 to 200856), and XbaI-P (bases 200391 to 206314) DNA fragments, respectively (Oram et al., 1982; Jones et al., 1991). pUS7/US3 contains the 1.7-kb PstI-PstI HCMV fragment (bases 194741 to 196447 in pIBI30 vector [International Biotechnologies, Inc.]) derived from pHind-G and pHind-X.

To replace HCMV ORFs US11 through IRS1 by β-glucuronidase (i.e. RV7186; FIG. 3), pBgdUS11/IRS1 are constructed. Sequentially, this plasmid contains the 1.8-kb fragment PstI-XbaI fragment (bases 200391 to 202207; containing US13, US12, and US11 promoter sequences; from pXba-P), β-glucuronidase, a 288-b SV40 fragment containing the early and late polyadenylation signals (from pRcCMV [Invitrogen]), and the 1.7-kb NcoI-NcoI fragment (bases 188062 to 189763; containing J1I to IRL1 sequences; from pHind-G).

To replace HCMV ORFs US11 through US2 by β-glucuronidase (i.e. RV798; FIG. 3), pBgdUS11/US2 are constructed. Sequentially, this plasmid contains the 1.8-kb fragment PstI-XbaI fragment (bases 200391 to 202207; containing US13, US12, and US11 promoter sequences; from pXba-P), β-glucuronidase, a 255-b fragment containing the US10 polyadenylation signal (bases 199021 to 199276; from pHind-X), and the 1.3-kb NheI-ApaI fragment (bases 192033 to 193360; containing C-terminal US2 to IRS1 sequences; from pHind-G).

To replace HCMV ORFs US11 through US6 by β-glucuronidase (i.e. RV35; FIG. 3), pBgdUS11/US6 was constructed. Sequentially, this plasmid contains the 1.8-kb PstI-XbaI fragment (bases 200391 to 202207; containing US13, US12, and US11 promoter sequences; from pXba-P), β-glucuronidase, and the 1.5-kb HpaI-SstII fragment (bases 194062 to 195589; containing C-terminal US6 to US3 sequences; from pHind-G). Replacement of HCMV ORFs US11–US10, or ORF US11 (singly), by β-glucuronidase (i.e. RV67 and RV699, respectively) were described previously (Jones et al., 1991).

To replace HCMV ORFs US9 through IRS1 by β-glucuronidase (i.e. RV7181; FIG. 3), pBgdUS9/IRS1 was constructed. Sequentially, this plasmid contains the 1.1-kb SalI-ApaI fragment (bases 199021 to 200171), the 351-b SV40 early promoter (from pRcCMV), β-glucuronidase, the 288-b SV40 polyadenylation signal fragment, and the 1.7-kb NcoI-NcoI fragment (bases 188062 to 189763; containing J1I to IRL1 sequences; from pHind-G).

To replace HCMV ORFs US6 through IRS1 by β-glucuronidase (i.e. RV7177; FIG. 3), pBgdUS6/IRS1 was constructed. Sequentially, this plasmid contains the 1.7-kb NcoI-NcoI fragment (bases 188062 to 189763; containing IRL1, J1I, and IRS1 promoter sequences; from pHind-G), β-glucuronidase, the 255-b fragment containing the US10 polyadenylation signal (bases 199021 to 199276; from pHind-X), and the 1.8-kb BsmI-SauI fragment (bases 196222 to 198030; containing US7 to C-terminal US9 sequences; from pHind-X).

To replace HCMV ORFs US3 and US2 by β-glucuronidase (i.e. RV47; FIG. 3), pBgdUS3/US2 was constructed. Sequentially, this plasmid contains the 1.7-kb PstI-PstI fragment (bases 194741 to 196447), a 180-b SmaI-HaeIII fragment containing the HSV-1 gH promoter (McKnight, 1980), β-glucuronidase, the 255-b US10 polyadenylation signal fragment, and the 1.3-kb NheI-ApaI fragment (bases 192033 to 193360; containing C-terminal US2 to IRS1 sequences; from pHind-G).

To replace HCMV ORF US1 by β-glucuronidase (i.e. RV5122; FIG. 3), pBgdUS1 was constructed. Sequentially, this plasmid contains the 1.8-kb AatII-SstI fragment (bases 190884 to 192648; containing IRS1 and US1 C-terminal sequences; from pHind-G), a 180-b SmaI-HaeIII fragment containing the HSV-1 gH promoter (McKnight, 1980), β-glucuronidase, the 255-b US10 polyadenylation signal fragment, and the 1.6-kb SphI-SphI fragment (bases 192934 to 194544; containing US2 and C-terminal US3 sequences; from pHind-G).

To replace HCMV ORF IRS1 by β-glucuronidase (i.e. RV46; FIG. 3), pBgdIRS1 was constructed. Sequentially, this plasmid contains the 1.7-kb NcoI-NcoI fragment (bases 188062 to 189763; containing IRL1, J1I, and IRS1 promoter sequences; from pHind-G), β-glucuronidase, the 255-b fragment containing the US10 polyadenylation signal (bases 199021 to 199276; from pHind-X), and the 1.2-kb NarI-XhoI fragment (bases 191830 to 193003; containing C-terminal IRS1 and US1 sequences; from pHind-G). To delete HCMV ORFs US11 through US2 without insertion of a reporter gene (i.e. RV799; FIG. 3), pdUS11/US2 was constructed. Sequentially, this plasmid contains the 1.8-kb fragment PstI-XbaI fragment (bases 200391 to 202207; containing US13, US12, and US11 promoter sequences; from pXba-P), β-glucuronidase, 65-b NruI-ApaI fragment containing the US10 polyadenylation signal (bases 199021 to 199086; from pHind-X), and the 1.3-kb NheI-ApaI fragment (bases 192033 to 193360; containing C-terminal US2 to IRS1 sequences; from pHind-G).

Isolation of recombinant mutant HCMV. Creation and isolation of recombinant mutant HCMV is done as described previously (Jones et al., 1991; Jones and Muzithras, 1992). HFF cells are split so that they are 70–80% confluent on the day of transfection. The cells are trypsinized and suspended to $5.6 \times 10^6$ cells per ml in DMEM/10% FCS/25 mM HEPES. The DNA is transfected using a modified calcium phosphate co-precipitation technique. 1.5 µg of infectious HCMV DNA and 2.5 µg of linearized plasmid DNA are mixed in the calcium chloride solution (300 µl containing 10 mM Tris pH 7.0/250 mM calcium chloride) and chilled on ice. To initiate the co-precipitation, the DNA is removed from the ice and 300 µl 2× HeBS pH 6.95 (at room temperature; 1× HeBS is 19.2 mM HEPES, 137 mM NaCl, 5 mM KCl, 0.8 mM sodium phosphate, 0.1% dextrose) is added dropwise with gentle mixing. After 1.5 min, the precipitate is placed on ice (to prevent further precipitate from forming). The precipitate is mixed with $3 \times 10^6$ cells (in suspension) and placed in a 82 mm tissue culture plate. After 6 h at 37° C., the media is removed and the cells are shocked with 20% DMSO in 1× HeBS for 2 min. The cells are washed twice with PBS and growth media is added. The media is changed every 4–7 days. After 14 days, viral plaques are observed and the cells are overlaid with 0.5% agarose in DMEM containing 150 µg/ml X-gluc (5-bromo 4-chloro 3-indol 1-glucuronide; Biosynth). Blue plaques (i.e. β-glucuronidase-positive mutant virus plaques) are picked several days after adding the overlay. Recombinant viruses were plaque purified three times. HCMV mutant RV799 is β-glucuronidase-negative and is isolated using a modification of the above procedure. In this case, β-glucuronidase-positive HCMV mutant RV134 is the parent virus (Jones et al., 1991). Thus, RV134 genomic DNA is used instead of wild-type strain AD169 DNA in the transfections. Primary plaques appearing on the primary transfection plates are picked at random and replated on HFF cells. After 10 days, the media is removed and the infected cells are overlaid with X-gluc-containing agarose as described above. In this case, white plaques (β-glucuronidase-negative mutant virus plaques) are picked 4 days later and plaque purified. The proper genomic organization of each of HCMV mutants is verified by DNA blot hybridization analysis as described previously (Jones et al., 1991). Antibodies. Rabbit polyclonal antisera reactive with HCMV US11 proteins and HCMV UL80 proteins are described previously (Jones et al., 1991; 1994). Murine monoclonal antibodies W6/32, specific for a conformation-dependent epitope on the heavy chain of human MHC class I proteins, and Ber-T9, specific for the human transferrin receptor, are purchased. Murine monoclonal antibody TP25.99 (D'Urso et al., 1991), specific for a conformation-independent epitope on the heavy chain of human MHC class I proteins, is obtained from Dr. S. Ferrone (Department of Microbiology, New York Medical College, Valhalla, N.Y.). Murine monoclonal antibody 9221, specific for the HCMV IE1 protein, is purchased from Dupont.

Radiolabeling and immunoprecipitation of infected cell proteins. Pulse-chase radiolabeling is done according to standard protocol (Sambrook et al., 1989). HCMV-infected HFF cells (multiplicity of infection equals five) is pulse-labeled with 200 µCi of [$^{35}$S] methionine and [$^{35}$S]cysteine (NEN-DuPont) per ml in methionine/cysteine-free Dulbecco's modified Eagle medium (DMEM) at the indicated time period postinfection. The radioactive media is removed, the cells washed twice in complete DMEM, and chases are done for the indicated time in complete DMEM. Proteins are extracted using triple detergent lysis buffer (Sambrook et al., 1989). The cleared protein extracts (supernatant after centrifugation for 5 min at 15000×g and 4° C.) are retained for immunoprecipitation according to standard protocol (Sambrook et al., 1989). Proteins binding to antibodies are pelleted using protein A sepharose (Pharmacia). For immunoprecipitations of the human transferrin receptor, rabbit anti-mouse IgG (Pierce) are added prior to protein A sepharose. The washed immunoprecipitates were boiled in the presence of 2-mercaptoethanol and electrophoresed in denaturing polyacrylamide gels. The gels are fixed and soaked in 1M sodium salicylate fluor (Sambrook et al., 1989) prior to drying and autoradiography.

Immunofluorescence. Immunofluorescence assays are done according to standard protocol (Harlow, 1989). All procedures are done in 60 mm tissue culture plates. Briefly, infected or uninfected HFF cells were fixed with 4% paraformaldehyde and permeabilized with 0.2% TRITON X-100™ (where indicated). After adding 3% bovine serum albumin in phosphate-buffered saline, the cells are held overnight at 4° C. The cells are treated sequentially with the following antisera, each for 30 min at room temperature: 10% HCMV-negative human serum (to block any Fc receptors); the indicated primary antibody; and FITC-conjugated anti-mouse or anti-rabbit IgG, as appropriate.

EXAMPLE 2

Figure 2A:
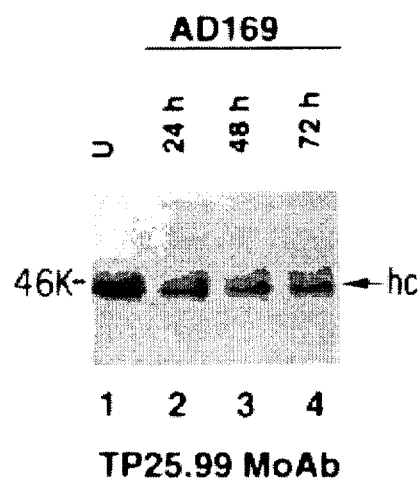
FIGS. 2A–2C. Expression of MHC class I heavy chains in HCMV wild-type strain AD169-infected cells.
Figure 2C:
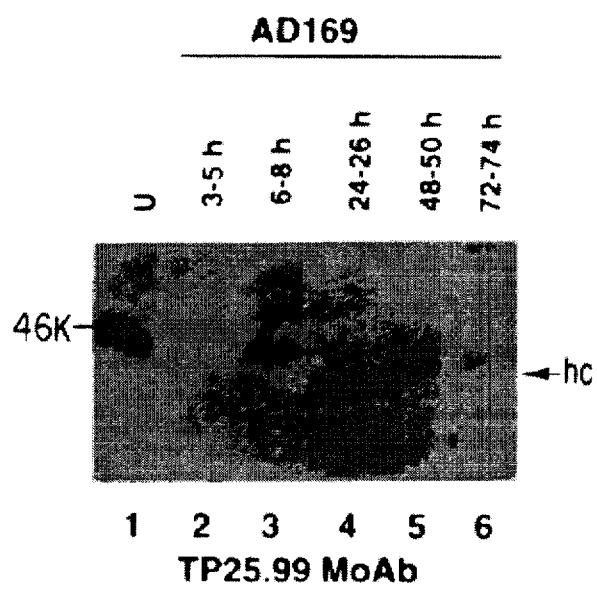
Figure 2B:
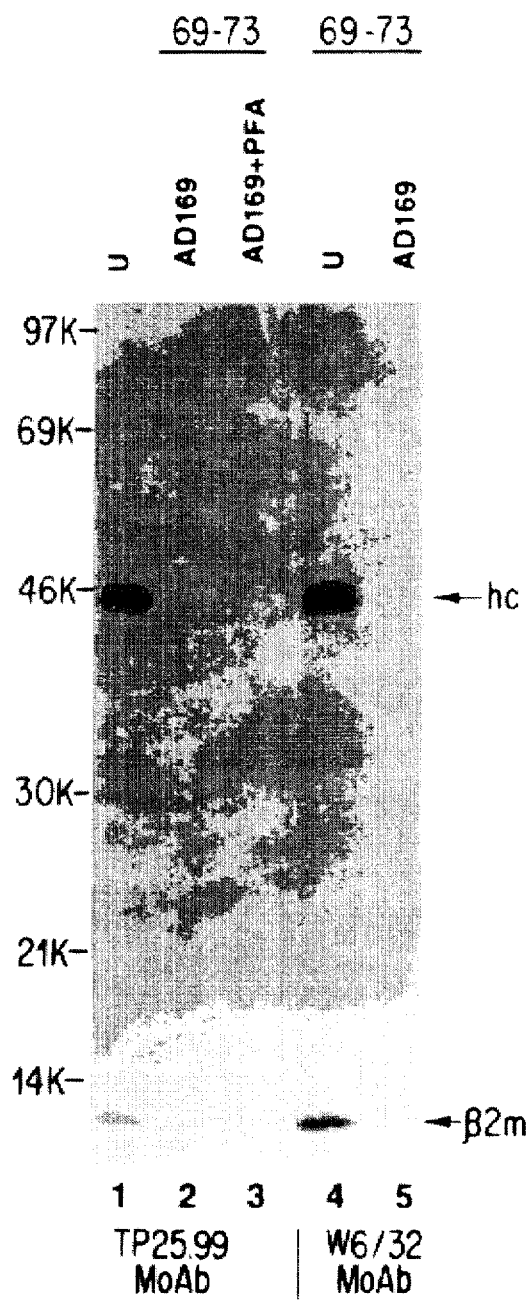
Figure 3A:
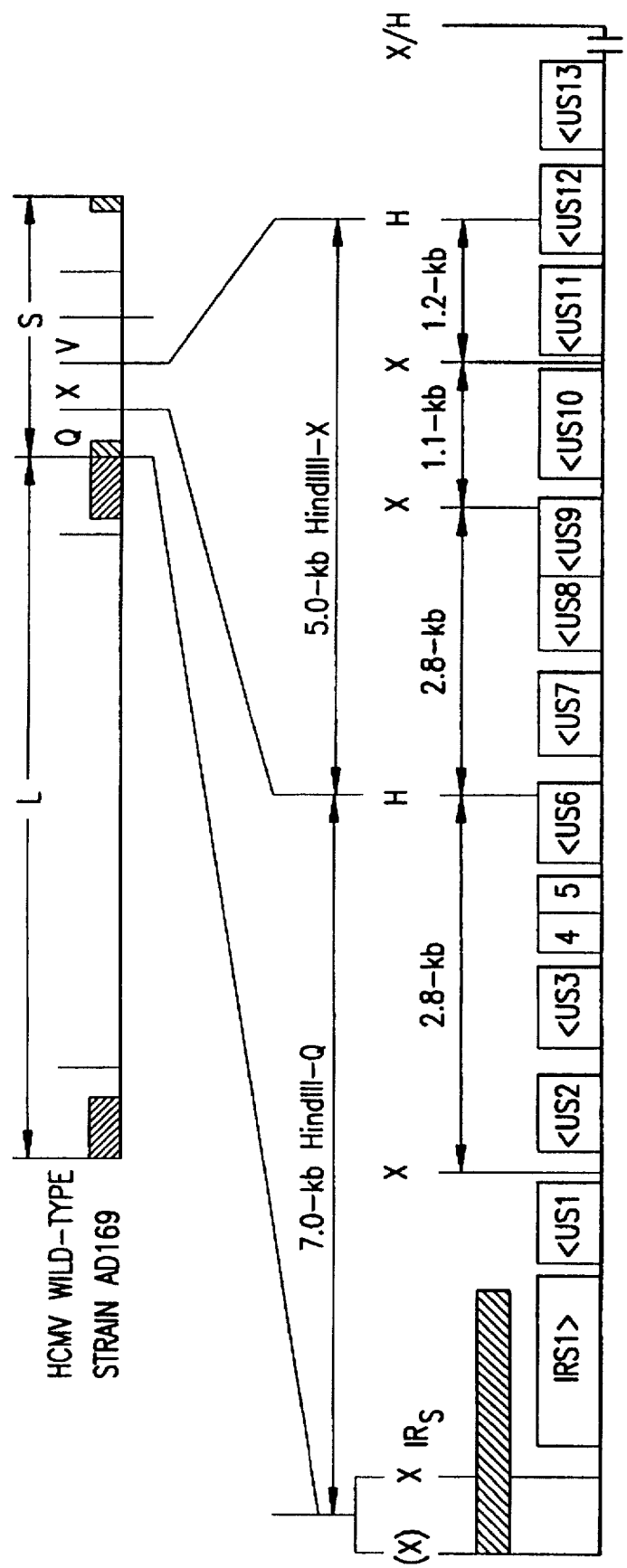
Figure 3B:
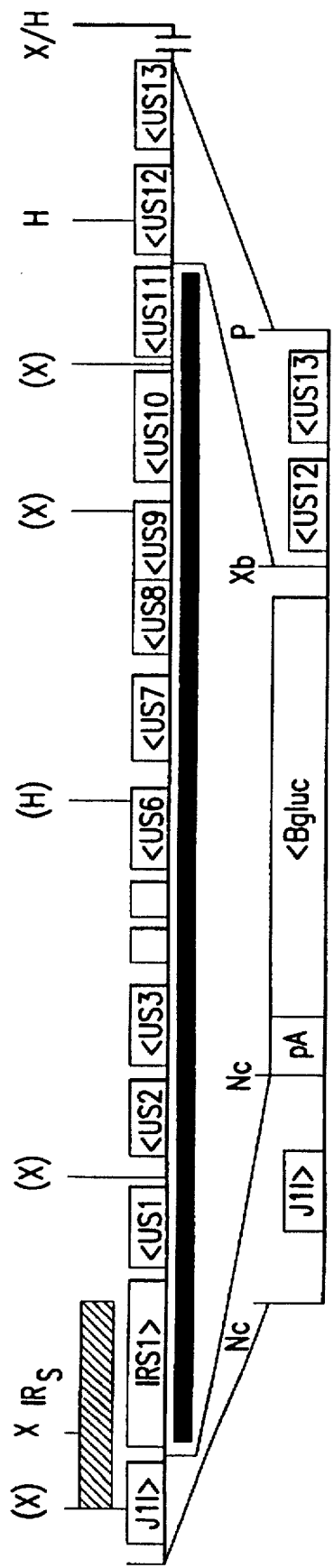
Figure 3C:
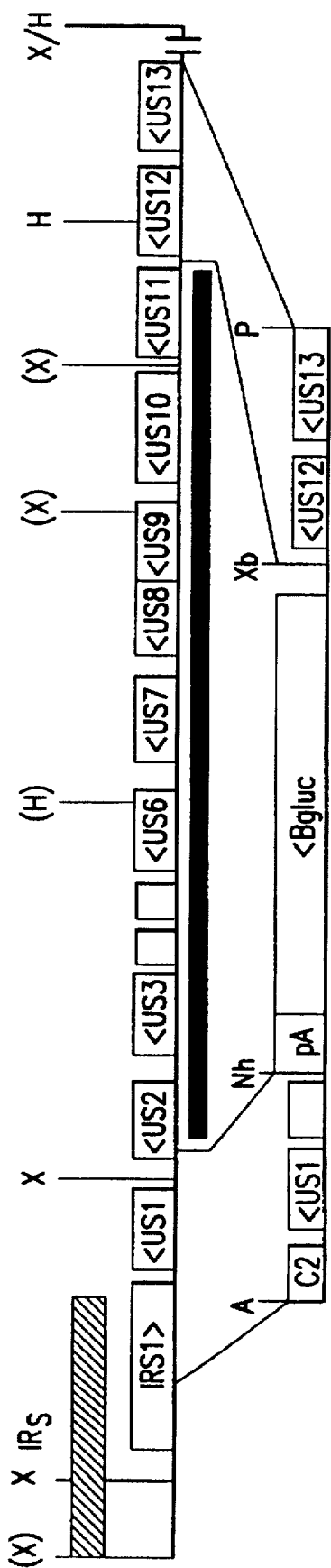
Figure 3D:
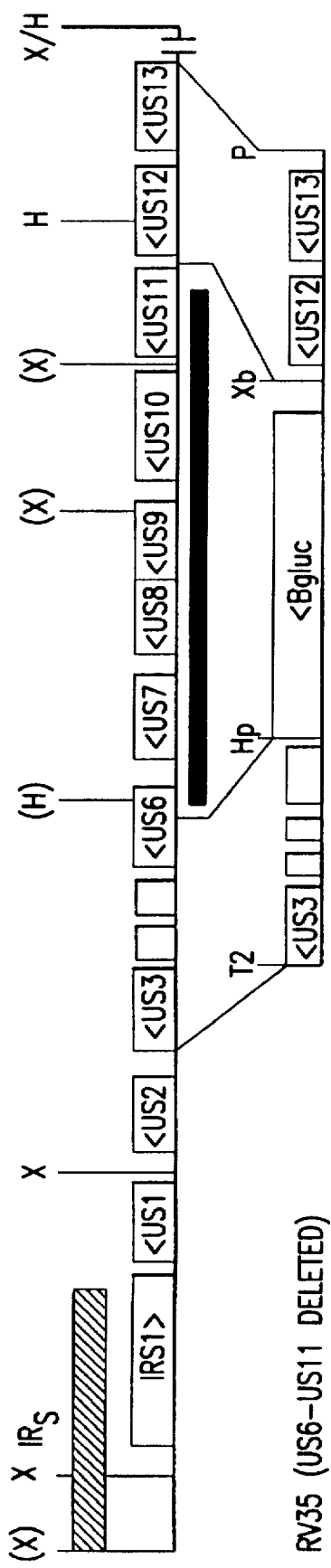
Figure 3E:
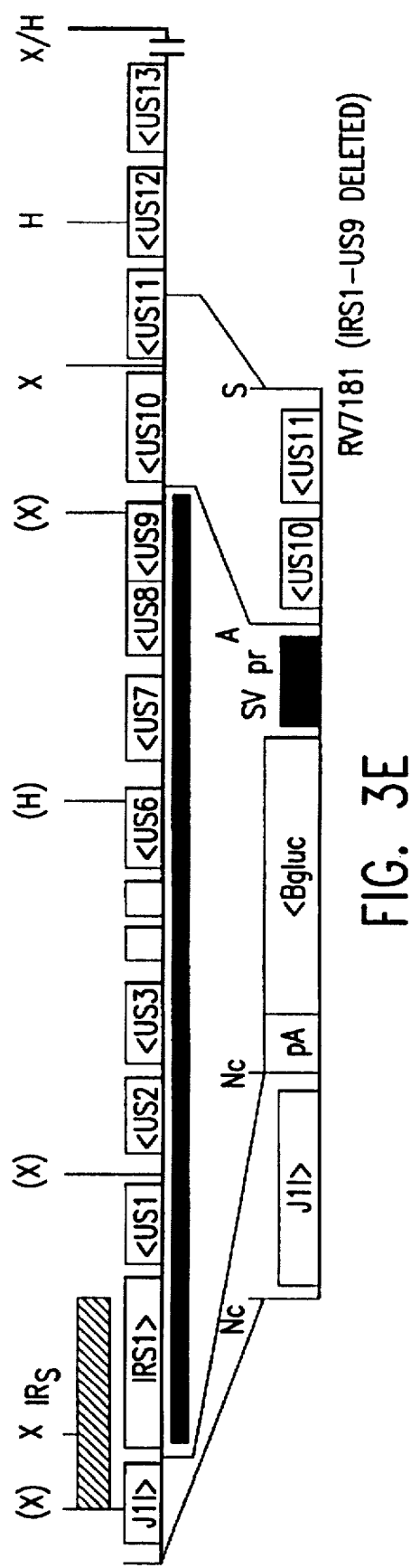
Figure 3F:
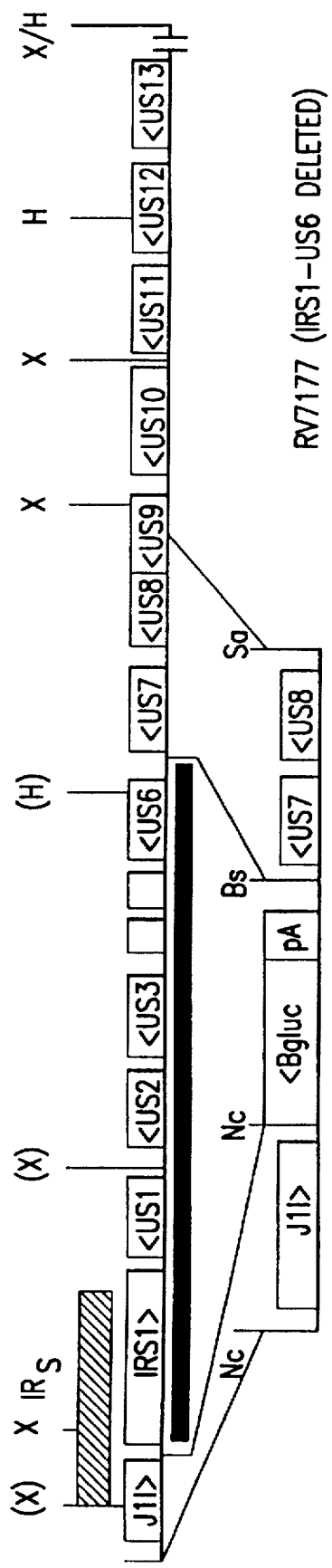
Figure 3G:
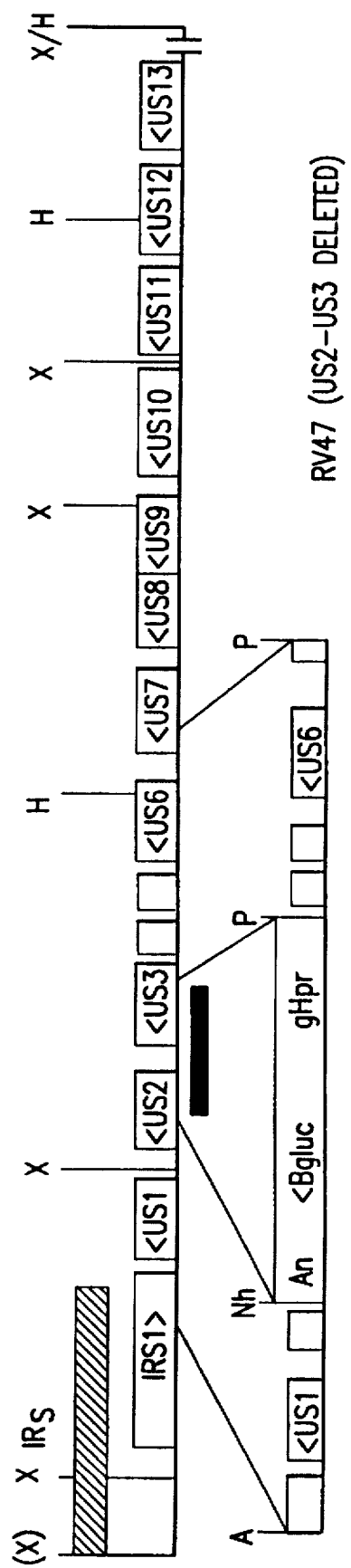
Figure 3J:
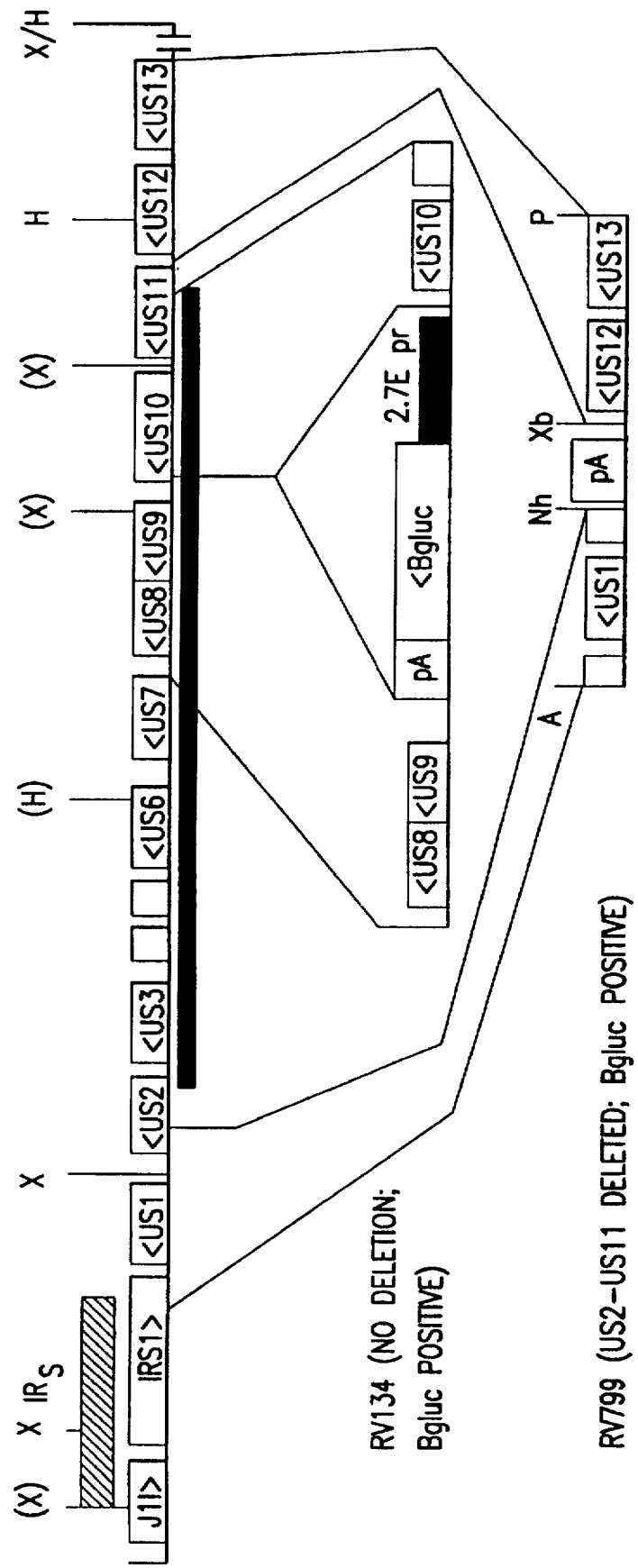

Class I down regulation in HCMV wild-type-infected human fibroblasts. We sought to ascertain the timing and nature of MHC class I heavy chain down regulation in the present invention's human foreskin fibroblast (HFF) cell culture system. By flow cytometry, HCMV strain AD169 wild-type-infected HFF cells are significantly reduced in the expression of class I heavy chains on their cell surface at late times postinfection (i.e. 72 h) using the conformation-dependent class I monoclonal antibody W6/32 (FIG. 1). In western analyses using the conformation-independent class I monoclonal antibody (TP25.99), it is demonstrated that the steady state level of class I protein is also reduced at late times postinfection (FIG. 2A). Because viral peptides are presented at the cell surface by class I complexes assembled after infection, we sought to assess the status of class I proteins synthesized at various times postinfection by immunoprecipitation of metabolically radiolabeled proteins. As shown in FIG. 2B, reduction in expression of class I heavy chains is detected both in the presence and absence of the viral DNA synthesis inhibitor, phosphonoformate. This indicates that viral immediate-early or early gene functions are sufficient for heavy chain reduction. In addition, it is demonstrated that heavy chain down regulation was detected at very early times postinfection: 3 h (FIG. 2C). Since this effect is observed using the conformation-independent antibody, the reduction reflects overall levels of newly synthesized heavy chains.

Figure 4A:
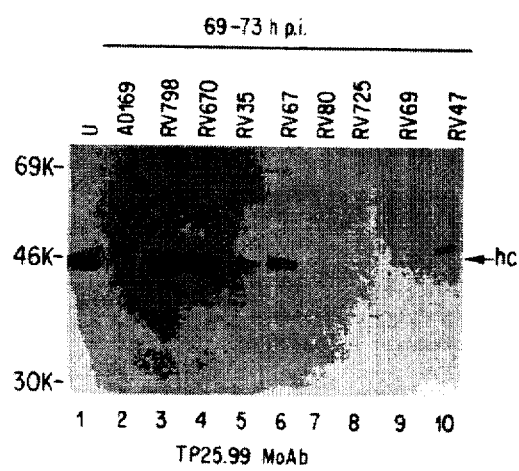
FIGS. 4A–4C show the analysis of heavy chain expression in cells infected with HCMV mutants. HFF cells were uninfected (U) or infected with the indicated virus (multiplicity of infection of 5 PFU/cell) and radiolabeled for 4 h at late times postinfection (69–73 h). Proteins were harvested immediately after radiolabeling.
Figure 4C:
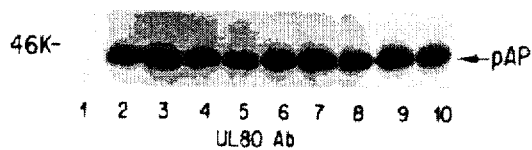
Figure 4B:
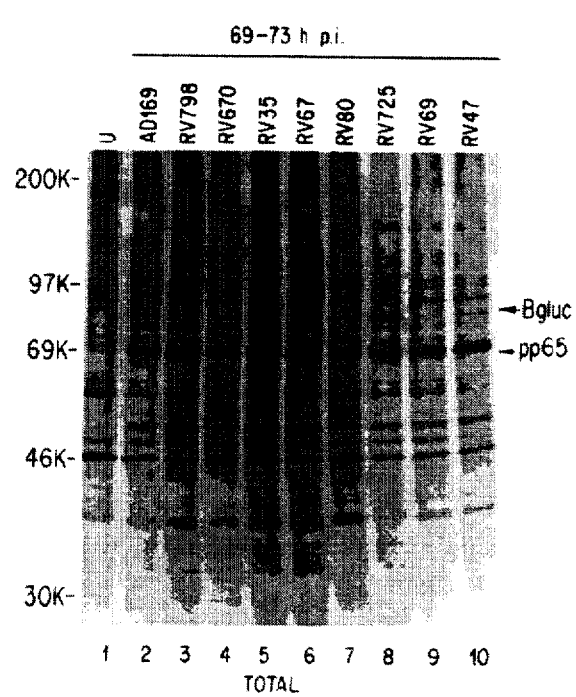

Screening of HCMV mutants for the loss of MHC class I down regulation. Several previously constructed HCMV deletion mutants, representing 18 nonessential ORFs (UL33, UL81, IRS1, US1–US13, US27–US28, and TRS1), are screened for heavy chain expression by flow cytometry and immunoprecipitation analyses. Only RV670, a mutant deleted of a 9-kb region within the S component of the HCMV genome (Jones and Muzithras, 1992), does not retain the wild-type down regulation phenotype (FIG. 4A). This mutant is deleted of at least 11 ORFs, IRS1 through US11 (except for US10), which includes the US6 family of genes (US6–US11) which putatively encode glycoproteins (Chee et al., 1990). To confirm this observation, two additional independently derived mutants which have the same deletion as RV670 and a new mutant, RV7186, deleted of the entire IRS1–US11 region (FIG. 3) are tested. Each is phenotypically identical to RV670 and stably expressed class I heavy chains. Previously, we constructed HCMV mutants deleted of US6 family ORFs, either individually or in groups (Jones and Muzithras, 1992), and similar deletion mutants within the adjacent IRS1–US3 region. By immunoprecipitation using the conformation-independent antibody, all of these mutants are shown to retain the ability to down regulate class I heavy chains (FIG. 4A) at late times postinfection in HFF cells. Control experiments indicate that radiolabeling is equivalent between the different infected cell cultures (FIG. 4B) and that infection proceeded to late times equally, as judged by pp65 (FIG. 4B) and UL80 protein (FIG. 4C) expression. These data indicate: (i) that more than one viral gene is sufficient for the reduction in class I heavy chains; or (ii) gene(s) between US3 and US6, deleted in RV670 and RV7186 but not the other mutants, is required for the phenotype.

Identification of a 7-kb region of the HCMV genome required for MHC class I down regulation. To further localize the region containing gene(s) involved in MHC class I heavy chain down regulation, additional HCMV replacement mutants containing deletions of multiple genes within the IRS1–US11 gene region are created (FIG. 3). One of these mutants, RV798, is deleted of genes from US2–US11. In HFF cells infected by RV798 and analyzed at late times postinfection, MHC class I heavy chains are not down regulated as they are in wild-type strain AD169-infected cells (FIG. 4A); in fact, a slight stimulation is observed. Several independently-derived deletion mutants identical to RV798 were examined similarly: all lacked the ability to down regulate class I heavy chains. To further confirm that the 7-kb HCMV US2–US11 region contains the gene(s) required for heavy chain down regulation, mutant RV799 is constructed which has the identical US2–US11 deletion as RV798, but is created by a different strategy. RV798 is derived from wild-type strain AD169 by inserting a β-glucuronidase marker gene in the place of US2–US11. In contrast, the parent of RV799 is RV134, a mutant which is β-glucuronidase-positive since it has a β-glucuronidase expression cassette inserted within the US9–US10 intergenic region (Jones et al., 1991). To create RV799, a plasmid is designed which upon recombination with the RV134 genome would simultaneously delete US2–US11 and the β-glucuronidase expression cassette (FIG. 3). The proper RV799 HCMV mutant is isolated as a white plaque in the presence of the β-glucuronidase substrate, since it β-glucuronidase-negative. RV799, but not the RV134 parent, is phenotypically identical to RV798 (FIG. 5) Thus, since RV798 and RV799 are created by different strategies using parents which retained the ability to down regulate MHC class I heavy chains, this confirms that the gene(s) required for the phenotype are located within the 7-kb US2–US11 region (bases 193119–200360).

Figure 6:
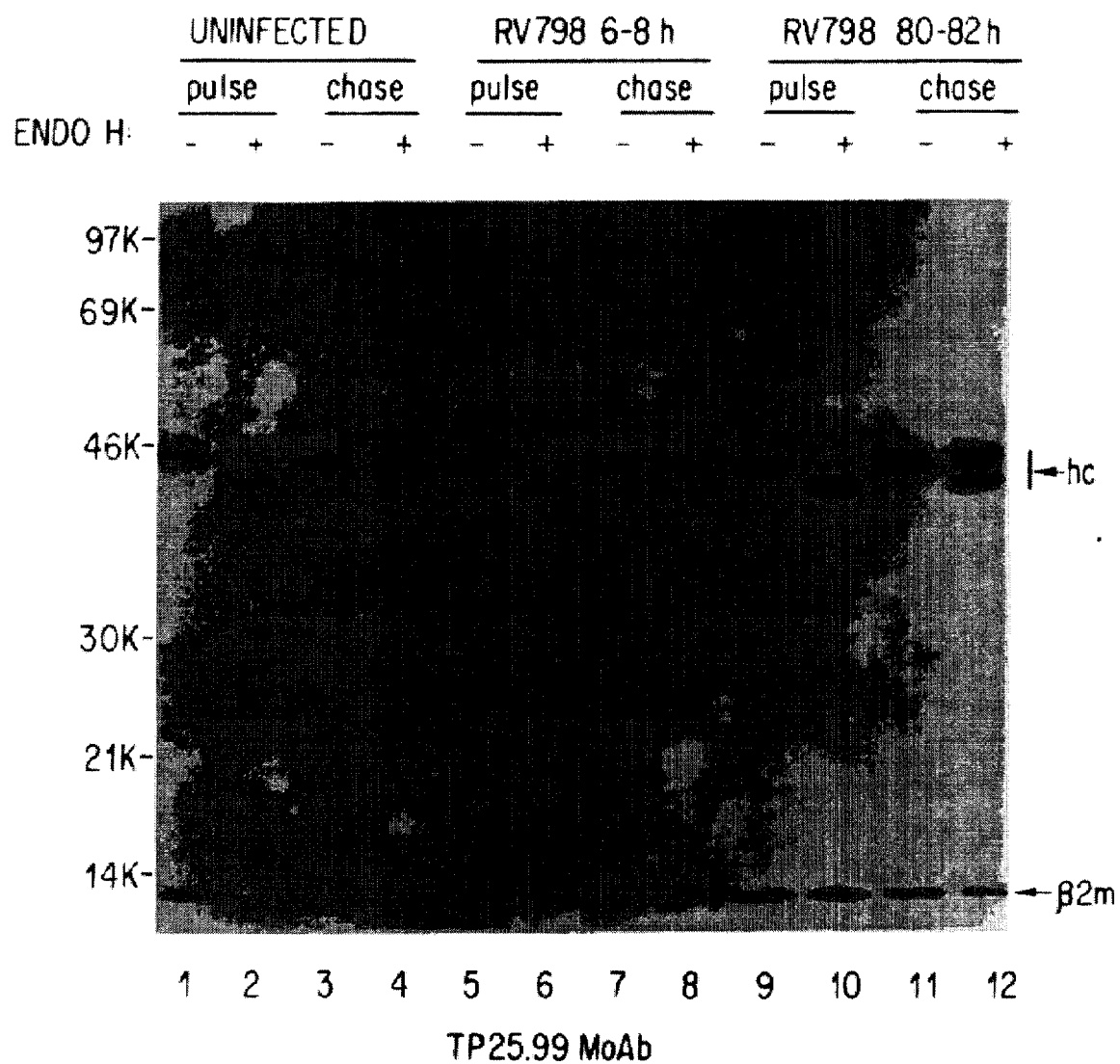
FIG. 6 is a radiograph showing the endoglycosidase H sensitivity of class I heavy chains synthesized in RV798-infected cells. HFF cells were infected with RV798 (multiplicity of infection of 5 PFU/cell) and radiolabeled for 2 h at early times (6–8 h) or late times (80–82 h) postinfection. For comparison purposes, uninfected cells were radiolabeled for 2 h. Proteins were harvested either immediately after radiolabeling (pulse) or after a 2 h chase (chase) in complete unlabeled media. Class I heavy chains were immunoprecipitated using TP25.99 murine monoclonal antibody. Immunoprecipitated protein were incubated for 6 h either in the presence (+) or absence (−) of 1.5 mU of endoglycosidase H, prior to SDS-polyacrylamide gel electrophoresis and fluorography.
Figure 8A:
FIGS. 8A–8D are photographs which show localization of US11 gene product (gpUS11) in infected cells by immunofluorescence. HFF cells were uninfected or infected with either AD169 wild-type or RV699 (deleted of the US11 gene) at a multiplicity of infection of 5 PFU/cell. After 8 h, uninfected and infected cells were fixed with 4% paraformaldehyde. Some cells were then permeabilized with 0.2% TRITON X-100™ (alkylaryl polyether alcohol). The primary antibody was rabbit polyclonal antisera raised against a US11 fusion protein (Jones and Muzithras, 1991). Fluorescence was visualized through a Zeiss microscope.
Figure 8B:
Figure 8C:
Figure 8D:
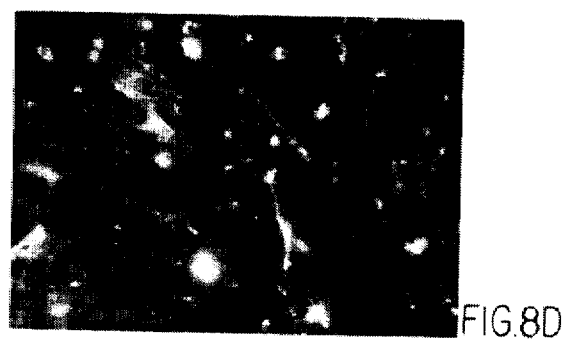

To determine whether the proper surface expression of class I heavy chains occurred at late times postinfection with either RV798 or RV799, immunofluorescence assays are done. Using either the conformation-dependent (W6/32) or conformation-independent (TP25.99) monoclonal antibodies, surface expression of MHC class I heavy chains is detected in uninfected and RV798- and RV799-infected HFF cells, but not wild-type AD169-infected HFF cells. Proper maturation of class I heavy chains in uninfected cells yields endoglycosidase H resistant molecules. In contrast, class I heavy chains synthesized in AD169-infected cells are reported to be entirely endoglycosidase H sensitive (Beersma et al., 1993). As shown in FIG. 6, class I heavy chains synthesized in RV798-infected HFF cells, either at early or late times postinfection, are converted to the mature endoglycosidase H-resistant form at a rate similar to those synthesized in uninfected cells. Taken together, these data indicate that MHC class I synthesis, processing, and surface expression are not impaired in cells infected with these HCMV mutants. Furthermore, the results indicate that the 7-kb region containing US2–US11 genes contain one or more genes required for heavy chain down regulation by HCMV.

Two subregions within the US2–US11 gene region contain genes which are involved in class I heavy chain down regulation. The region of the HCMV genome deleted in RV35 is from US6–US11, and US2–US11 in RV798 (FIG. 3). In RV35-infected HFF cells, MHC class I heavy chains are down regulated, but in RV798-infected cells they are not (FIG. 4A). This data indicates that one or more genes involved in heavy chain down regulation maps within the 2-kb subregion from ORF US2 through US5 (subregion A; bases 193119–195607). To determine if this 2-kb subregion is required for class I heavy chain down regulation, HCMV replacement mutants RV7181 and RV7177 are examined. HCMV ORFs IRS1–US9 and IRS1–US6 are deleted, respectively, in these mutants; hence, subregion A is absent from both mutants. Experiments in infected HFF cells at late times postinfection indicates that both mutants retained the ability to efficiently down regulate class I heavy gene expression (FIG. 7). Therefore, when present in the HCMV genome, gene(s) within subregion A are sufficient for reduction of MHC expression (e.g. RV35), although their presence is not required for the phenotype. Furthermore, the cumulative data indicate that there are no HCMV genes within the identified 7-kb US2–US11 region (i.e. the region deleted in RV798) which are absolutely required for efficient heavy chain down regulation in infected HFF cells, suggesting that gene(s) from another portion of the US2–US11 gene region are also sufficient for the phenotype at late times postinfection.

Evidence indicating that the US11 gene product is involved in MHC class I heavy chain down regulation. In HFF cells infected with mutant RV7181, deleted from IRS1–US9 (FIG. 3), MHC class I heavy chain expression is down regulated, in contrast to RV798-infected HFF cells (FIG. 7). This data suggests that a second subregion (subregion B), comprised of the US10 and US11 genes (bases 199083–200360), is involved in reduction of heavy chain expression. However, the expression of US10 from the context of the HCMV genome is not sufficient for heavy chain down regulation. HCMV mutant RV670 expresses US10 at steady-state levels similar to wild-type and is deleted of all of the other ORFs in the 7-kb US2–US11 gene region, but it does not cause down regulation of MHC class I heavy chains in infected HFF cells (FIGS. 2B and 4A).

US11 encodes a 32-kDa glycoprotein (gpUS11) containing N-linked, but not O-linked, carbohydrates which are completely sensitive to endoglycosidase H, indicating that the sugars are in the high mannose form. gpUS11 is detected throughout infection, beginning at very early times (i.e. 3 h) and continuing through late times postinfection. However, levels of gpUS11 in the infected cell are most abundant at approximately 8 h postinfection. To determine its location in the infected cell, rabbit polyclonal antisera (Jones and Muzithras, 1991) is used in immunofluorescence assays of wild-type strain AD169-infected cells. Uninfected and RV699-infected HFF cells are used as negative controls. RV699 is an HCMV mutant which is isogeneic with AD169, except for a deletion of the US11 ORF (Jones et al., 1991). In cells fixed and permeabilized at 8 h postinfection, cytoplasmic fluorescence which obscured definition of the nucleus is observed in AD169-infected HFF cells, but not in either negative control cells (FIG. 8). In general, the specific fluorescence is more intense in the perinuclear area. There is no specific fluorescence detected in non-permeabilized cells (FIG. 8). The fluorescence and endoglycosidase-H sensitivity data indicate that gpUS11 is not a cell surface glycoprotein. From the translated DNA sequence, gpUS11 is predicted to have hydrophobic domain near its N- and C-termini (Weston and Barrell, 1986) which are putative signal sequence and transmembrane domain, respectively. Thus, gpUS11 is associated with intracytoplasmic membranes, possibly the endoplasmic reticulum.

Figure 9A:
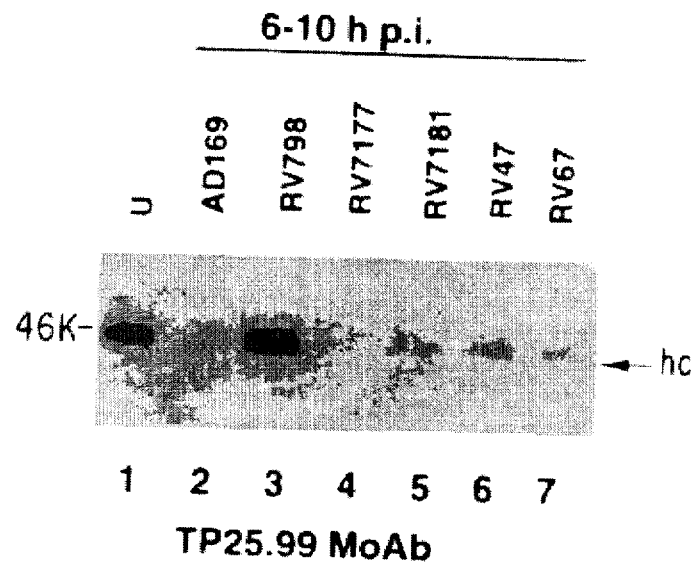
FIGS. 9A–9D show analysis of heavy chain expression in cells infected with HCMV mutants at early times postinfection. HFF cells were uninfected (U) or infected with the indicated virus (multiplicity of infection of 5 PFU/cell) and radiolabeled for 4 h from 6–10 h postinfection. Proteins were harvested immediately after radiolabeling.
Figure 9B:
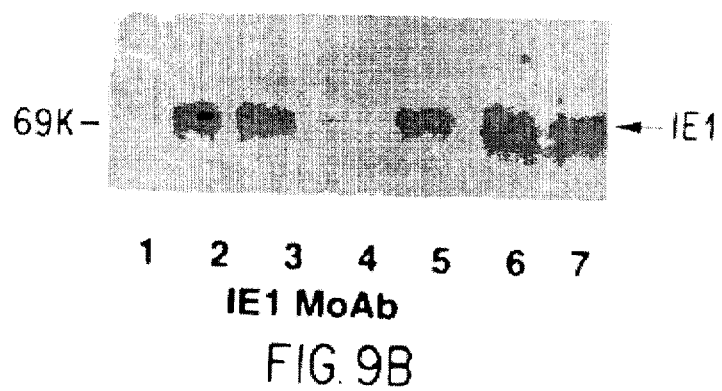
Figure 9C:
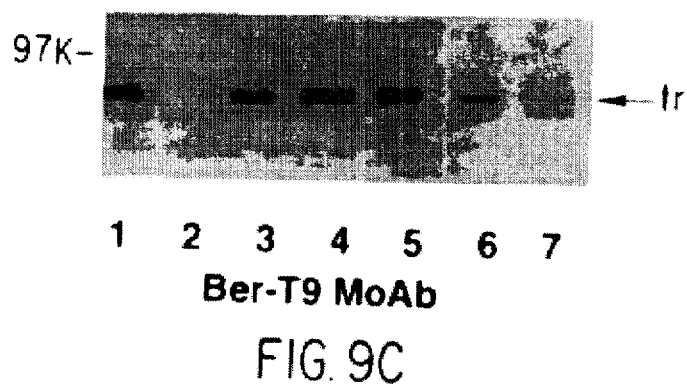
Figure 9D:
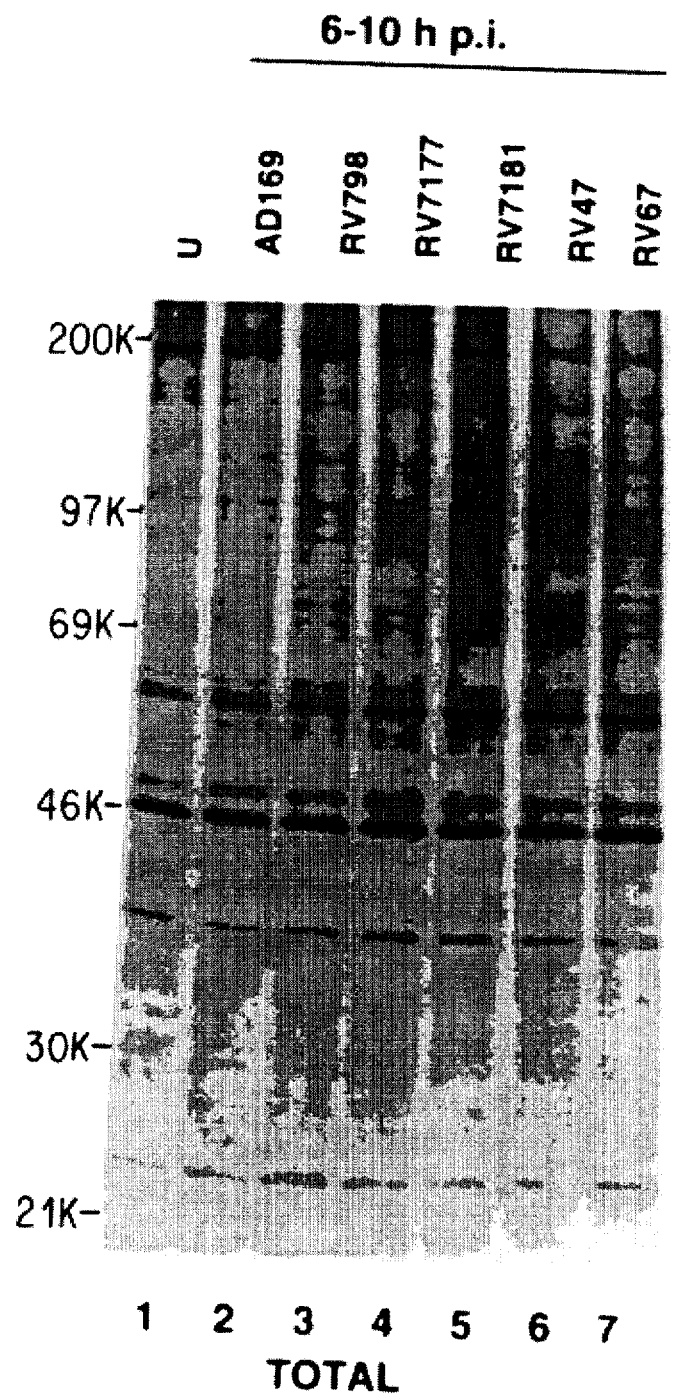
Figure 10:
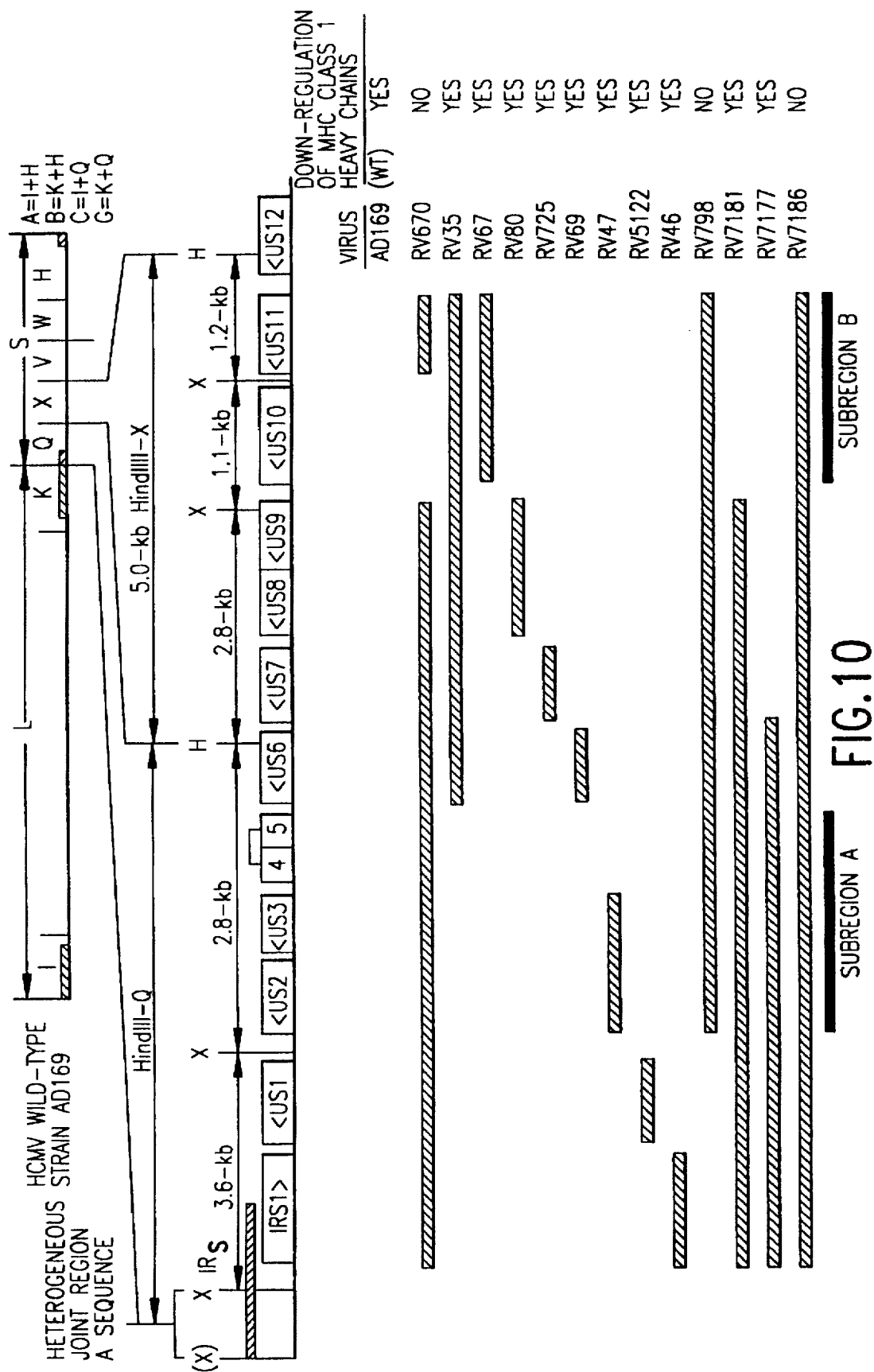
FIG. 10 provides a summary of MHC class I heavy chain expression data from HFF cells infected with wild-type and mutant HCMV.

Down regulation of MHC class I expression at early times postinfection by HCMV mutants. MHC class I expression in wild-type strain AD169-infected cells are shown to begin at very early times postinfection (FIG. 2C). To determine if any of the mutants are deficient for this early down regulation, immunoprecipitation experiments are performed using extracts from infected HFF cells radiolabeled from 6–10 h postinfection. The level of class I heavy chains are reduced during this early period postinfection in HFF cells with each of the mutants, except for RV798, the mutant deleted of the entire 7-kb US2–US11 region (FIG. 9A). Control experiments demonstrated that the different mutant-infected cells are equally infected and radiolabeled (FIGS. 9B and D). Expression of another cellular glycoprotein, the transferrin receptor, is not differentially affected by the various mutants (FIG. 9C). Thus, genes required for heavy chain down regulation at early times postinfection are the same as those necessary for reduction at late times postinfection. Moreover, expression of gene(s) from either subregion identified to be involved in down regulation of heavy chain expression at late times postinfection are sufficient for reduction at very early times postinfection.

EXAMPLE 3

Recombinant HCMV (RV798) Vaccine Preparation. HCMV vaccines are prepared using a method described previously (Elek and Stern, 1974). HCMV mutant RV798 is grown on MRC-5 human diploid lung fibroblasts (CCL171 [American Type Culture Collection]) or human foreskin fibroblasts (MRHF [BioWhittaker]). Cells are infected at a multiplicity of infection equal to one in Dulbecco's modified Eagle medium (DMEM) containing 5% calf serum and 5% fetal calf serum. After 24 h, the medium is removed and the cells washed three times with either Hank's balanced salt solution or Dulbecco's phosphate-buffered saline. Fresh DMEM medium without serum is added; the infected cells are incubated 4 days after the appearance of late viral cytopathic effect (usually 7 days postinfection). After a preclearing centrifugation step (6,000×gravity for 20 min at 18° C.), cell-free virus is pelleted by centrifugation at 15,500×gravity for 1 h at 18° C. The pelleted virus is resuspended in Dulbecco's phosphate-buffered saline containing 25% sorbitol and stored in aliquots at −70° C. The titer of RV798 vaccine stock is determined using standard procedures on human foreskin fibroblasts (Wentwork and French, 1970). The vaccine is administered by subcutaneous inoculation of approximately $10^3$–$10^7$ plaque forming units into the deltoid region of the upper arm, as described previously (Elek and Stern, 1974; Gehrz et al., 1980; Starr et al., 1981).

Figure 11A:
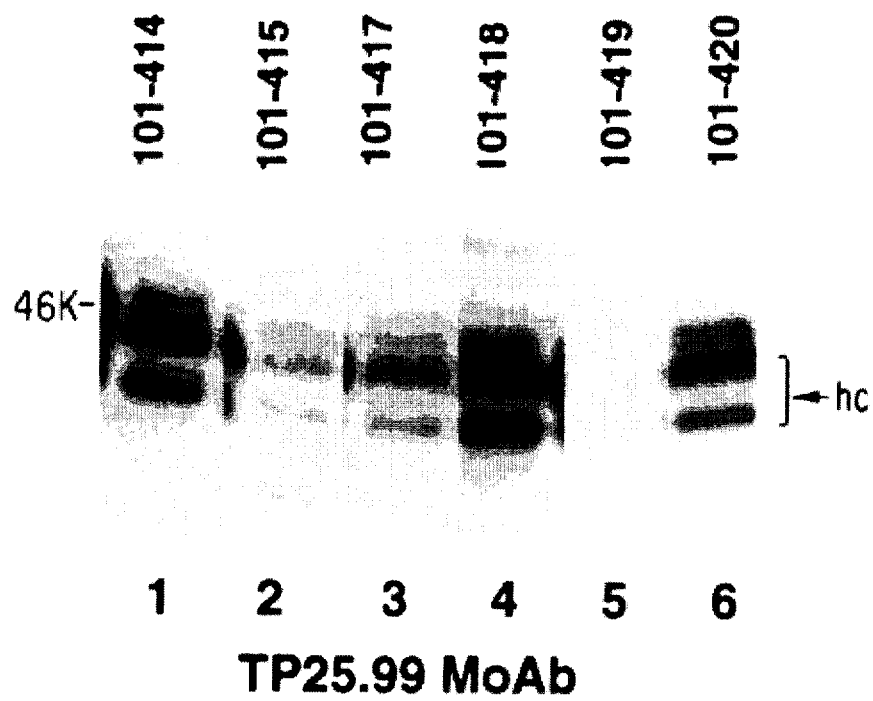
FIGS. 11A–11B are Western Blots of cell lines expressing the HCMV US11 gene. Uninfected human U373-MG astrocytoma cells stably transformed with a US11 expression plasmid were analyzed by Western Blot analysis for MHC class I heavy chain expression (FIG. 11A) and for US11 expression (FIG. 11B) using the TP25.99 monoclonal antibody and the US11 polyclonal antisera, respectively.
Figure 11B:
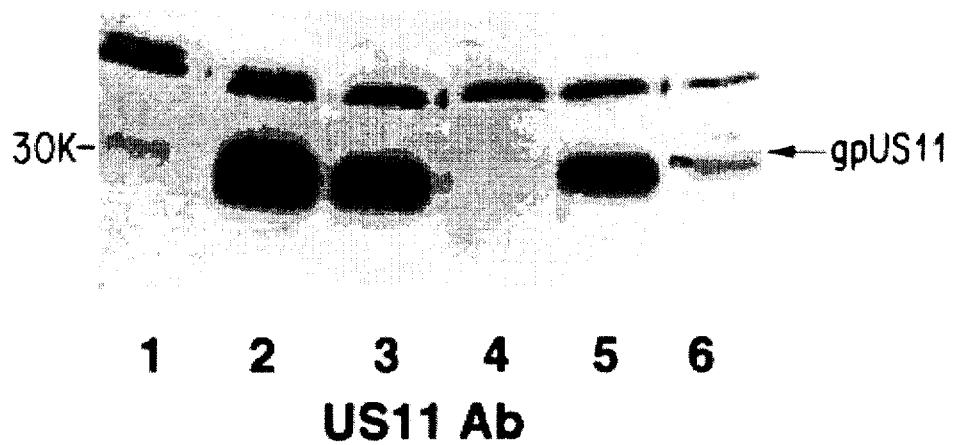

EXAMPLE 4 gpUS11 is sufficient for down regulation of MHC class I heavy chains. To determine if the US11 gene product, in the absence of any other viral gene products, is capable of causing heavy chain down regulation, the US11 coding region (bases 199716 to 200360 [Chee et al., 1990]) and some non-coding flanking sequences, encompassing bases 199683 to 200391, are cloned into a eukaryotic expression plasmid under the transcriptional control of the constitutive HCMV major immediate-early promoter-enhancer. Human U373-MG astrocytoma cells (HTB 17 [American Type Culture Collection]) are transfected with this plasmid (Sambrook et al, 1989) and stably transformed cells are selected in the presence of 0.375 µg/ml of puromycin, since the plasmid also encodes for the prokaryotic puromycin resistance gene. Clones are picked and expanded into cell lines. Those expressing gpUS11 are identified by western blot analysis; different cell lines expressed varying amounts of US11. MHC class I heavy chain expression in these cell lines is analyzed in a similar fashion. As shown in FIG. 11, expression of US11 is inversely correlated with the expression of class I heavy chains. These data prove that expression of HCMV US11 is sufficient for the down regulation of MHC class I heavy chain expression, in the absence of any other viral gene products.

REFERENCES

Alford, C. A., and W. J. Britt. 1990. Cytomegalovirus, p. 1981–2010. In D. M. Knipe and B. N. Fields (ed.), Virology, 2nd ed. Raven press, New York.

Anderson, M., S. Paabo, T. Nilsson, and P. A. Peterson. 1985. Impaired intracellular transport of class I MHC antigens as a possible means for adenoviruses to evade immune surveillance. Cell 43:215–222.

Beck, S., and B. G. Barrell. 1988. Human cytomegalovirus encodes a glycoprotein homologous to MHC class I antigens. Nature 331:269–272.

Beersma, M. F. C., M. J. E. Bijlmakers, and H. L. Ploegh. 1993. Human cytomegalovirus down regulates HLA class I expression by reducing the stability of class I H chains. J. Immunol. 151:4455–4464.

Browne, H., M. Churcher, and T. Minson. 1992. Construction and characterization of a human cytomegalovirus mutant with the UL18 (class I homolog) gene deleted. J. Virol. 66:6784–6787.

Browne, H., G. Smith, S. Beck, and T. Minson. 1990. A complex between the MHC class I homolog encoded by human cytomegalovirus and β2 microglobulin. Nature 347:770–772.

Burgert, H. G., and S. Kvist. 1985. An adenovirus type 2 glycoprotein blocks cell surface expression of human histocompatibility class I antigens. Cell 41:987–997.

Campbell, A. E., J. S. Slater. 1994. Down-regulation of major histocompatibility complex class I synthesis by murine cytomegalovirus early gene expression. J. Virol. 68:1805–1811.

Campbell, A. E., J. S. Slater, V. J. Cavanaugh, and R. M. Stenberg. 1992. An early event in murine cytomegalovirus replication inhibits presentation of cellular antigens to cytotoxic T lymphocytes. J. Virol. 66:3011–3017.

Chee, M. S., A. T. Bankier, S. Beck, R. Bohni, C. M. Brown, R. Cerny, T. Horsnell, C. A. Hutchinson, T. Kouzarides, J. A. Martignetti, E. Preddie, S. C. Satchwell, P. Tomlinson, K. Weston, and B. G. Barrell. 1990. Analysis of the protein-coding content of the sequence of human cytomegalovirus strain AD169. Curr. Top. Microbiol. Immunol. 154:125–169.

Colberg-Poley, A. M., L. D. Santomenna, P. P. Harlow, P. A. Benfield, and D. J. Tenney. 1992. Human cytomegalovirus US3 and UL36–38 immediate-early proteins regulate gene expression. J. Virol. 66:95–105.

del Val, M., K. Munch, M. Reddehasse, and U. Koszinowski. 1989. Presentation of CMV immediate-early antigen to cytotoxic T lymphocytes is selectively prevented by viral genes expressed in the early phase. Cell 58:305–315.

D'Urso, C. M., Z. Wang, Y. Cao, R. Tatake, R. A. Zeff, and S. Ferrone. 1991. Lack of HLA class I antigen expression by cultured melanoma cells FO-1 due to a defect in β2m gene expression. J. Clin. Invest. 87:284–292.

Elek, S. D., and H. Stern. 1974. Development of a vaccine against mental retardation caused by cytomegalovirus infection in utero. Lancet 1:1–5.

Gehrz, R. C., W. R. Christianson, K. M. Linner, K. E. Groth, and H. H. Balfour, Jr. 1980. Cytomegalovirus vaccine: specific humoral and cellular responses in human volunteers. Arch. intern. Med. 140:936–939.

Gilbert, M. J., S. R. Riddell, C-R. Li, and P. D. Greenberg. 1993. Selective interference with class I major histocompatibility complex presentation of the major immediate-early protein following infection with human cytomegalovirus. J. Virol. 67:3461–3469.

Gooding, L. R. 1992. Virus proteins that counteract host immune defenses. Cell 71:5–7.

Gretch, D. R., and M. F. Stinski. 1990. Transcription of the human cytomegalovirus glycoprotein gene family in the short unique component of the viral genome. Virology 174:522–532.

Jones, T. R., and Muzithras, V. P. 1991. Fine mapping of transcripts expressed from the US6 gene family of human cytomegalovirus strain AD169. J. Virol. 65:2024–2036.

Jones, T. R., and V. P. Muzithras. 1992. A cluster of dispensable genes within the human cytomegalovirus genome short component: IRS1, US1 through US5, and the US6 family. J. Virol. 66:2541–2546.

Jones, T. R., V. P. Muzithras, and Y. Gluzman. 1991. Replacement mutagenesis of the human cytomegalovirus genome: US10 and US11 gene products are nonessential. J. Virol. 65:5860–5872.

Jones, T. R., L. Sun, G. A. Bebernitz, V. P. Muzithras, H-J. Kim, S. H. Johnston, and E. Z. Baum. 1994. Proteolytic activity of human cytomegalovirus UL80 protease cleavage site mutants. J. Virol. 68: 3742–3752.

Jonjic, S., M. de Val, G. M. Keil, M. J. Reddehasse, and U. Koszinowski. 1988. A nonstructural viral protein expressed by a recombinant vaccinia virus protects against lethal cytomegalovirus infection. J. Virol. 62:1653–1658.

Mavromara-Nazos, P., M. Ackerman, and B. Roizman. 1986. Construction and properties of a viable herpes simplex virus 1 lacking coding sequences of the alpha 47 gene. J. Virol 60:807–812.

McKnight, S. L. 1980. The nucleotide sequence and transcript map of the herpes simplex virus thymidine kinase gene. Nucl. Acids Res. 8:5949–5964.

Oram, J. D., R. G. Downing, A. Akrigg, A. A. Dollery, C. J. Duggleby, G. W. G. Wilkinson, and P. J. Greenaway. 1982. Use of recombinant plasmids to investigate the structure of the human cytomegalovirus genome. J. Gen. Virol. 59:111–129.

Sambrook, J., E. F. Fritsch, and T. Maniatis. 1989. Molecular cloning: a laboratory manual, 2nd ed. Cold Spring Harbor Laboratory Press, Cold Spring Harbor, N.Y.

Schwartz, R. H. 1985. T lymphocyte recognition of antigen in association with gene products of the major histocompatibility complex. Ann. Rev. Immunol. 3:237–261.

Starr, S. E., J. P. Glazer, H. M. Friedman, J. D. Farquhar, and S. A. Plotkin. 1981. Specific cellular and humoral immunity after immunization with live Towne strain cytomegalovirus vaccine. J. Infect. Dis. 143:585–589.

Tenney, D. J., and A. M. Colberg-Poley. 1991. Human cytomegalovirus UL36–38 and US3 immediate-early genes: temporally regulated expression of nuclear, cytoplasmic, and polysome-associated transcripts during infection. J. Virol. 65:6724–6734.

Tenney, D. J., L. D. Santomenna, K. B. Goudie, and A. M. Colberg-Poley. 1993. The human cytomegalovirus US3 immediate-early protein lacking the putative transmembrane domain regulates gene expression. Nucl. Acids Res. 21:2931–2937.

Wentworth, B. B., and French, L. 1979. Plaque assay of cytomegalovirus strains of human origin. Proc. Soc. Exp. Biol., Med. 135:253–258.

Weston, K. 1988. An enhancer element in the short unique region of human cytomegalovirus regulates the production of a group of abundant immediate early transcripts. Virology 162:406–416.

Weston, K., and B. G. Barrell. 1986. Sequence of the short unique region, short repeats, and parts of the long repeats of human cytomegalovirus. J. Mol. Biol. 192:177–208.

Yamashita, Y., K. Shimokata, S. Mizuno, H. Yamaguchi, and Y. Nishiyama. 1993. Down-regulation of the surface expression of class I MHC antigens by human cytomegalovirus. Virology 193:727–736.

York, I. A., C. Roop, D. W. Andrews, S. R. Riddell, F. L. Graham, and D. C. Johnson. 1994. A cytosolic herpes simplex virus protein inhibits antigen presentation to CD8+ T lymphocytes. Cell 77:525–535.

Zinkernagel, R. M., and P. C. Doherty. 1980. MHC restricted cytotoxic T cells: studies on the biological role of polymorphic major transplantation antigens determining T cell restriction specificity. Adv. Immunol. 27:51–177.

What is claimed is:

1. A method of producing a cytomegalovirus which does not down regulate expression of major histocompatibility complex (MHC) class I expression upon infection of a cell, comprising the steps of:

(a) identifying one or more gene sequences in the region of the genome of the cytomegalovirus containing open reading frames IRS-1–US11 which down regulates the MHC class I expression; and (b) deleting the identified gene sequences from the genome of the cytomegalovirus.

2. The method of claim 1, wherein the identified gene sequences are from the region of the cytomegalovirus genome containing open reading frames IRS-1–US9 and US11.

3. The method of claim 1, wherein the identified gene sequences are from the region of the cytomegalovirus genome containing open reading frames US2–US11.

4. The method of claim 1, wherein the identified gene sequences are from the region of the cytomegalovirus genome containing subregion A, wherein subregion A comprises open reading frames US2–US5, and subregion B, wherein subregion B comprises open reading frames US10–US11.

5. The method of claim 4, wherein the identified gene sequence from subregion B consists of the open reading frame US11.

* * * * *

UNITED STATES PATENT AND TRADEMARK OFFICE
CERTIFICATE OF CORRECTION

PATENT NO. : 5,753,476
DATED : May 19, 1998
INVENTOR(S) : Thomas R. Jones, Ann E. Campbell It is certified that error appears in the above-identified patent and that said Letters Patent is hereby corrected as shown below:

On the title page, item [75] Inventors - change "Norfalk" to --Norfolk--.

Col. 2, line 7: change "registration" to --regulation--.

Signed and Sealed this

Twenty-second Day of December, 1998

Attest:

BRUCE LEHMAN

Attesting Officer     Commissioner of Patents and Trademarks